(12) United States Patent
Sugimoto

(10) Patent No.: US 8,348,829 B2
(45) Date of Patent: Jan. 8, 2013

(54) SCANNING ENDOSCOPE APPARATUS, SCANNING ENDOSCOPE, AND SCANNING ENDOSCOPE PROCESSOR

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 440 days.

(21) Appl. No.: 12/647,083

(22) Filed: Dec. 24, 2009

(65) Prior Publication Data
US 2010/0168515 A1 Jul. 1, 2010

(30) Foreign Application Priority Data

Dec. 26, 2008 (JP) ................................. 2008-331814
Dec. 26, 2008 (JP) ................................. 2008-331903

(51) Int. Cl.
*A61B 6/00* (2006.01)
(52) U.S. Cl. ................ 600/109; 600/473; 600/476
(58) Field of Classification Search ........... 600/101–183
See application file for complete search history.

(56) References Cited

U.S. PATENT DOCUMENTS

| | | | | |
|---|---|---|---|---|
| 4,786,965 A | * | 11/1988 | Yabe | 348/76 |
| 4,860,094 A | * | 8/1989 | Hibino et al. | 600/109 |
| 5,216,652 A | * | 6/1993 | Yoshio et al. | 369/44.37 |
| 6,294,775 B1 | * | 9/2001 | Seibel et al. | 250/208.1 |
| 6,845,190 B1 | | 1/2005 | Smithwick et al. | |
| 6,975,898 B2 | * | 12/2005 | Seibel | 600/473 |
| 7,068,878 B2 | * | 6/2006 | Crossman-Bosworth et al. | 385/25 |
| 2001/0055462 A1 | * | 12/2001 | Seibel | 385/147 |
| 2005/0020883 A1 | * | 1/2005 | Chatenever et al. | 600/173 |
| 2005/0052753 A1 | | 3/2005 | Kanai | |
| 2007/0035797 A1 | * | 2/2007 | Kanai | 359/212 |
| 2007/0197875 A1 | * | 8/2007 | Osaka | 600/173 |
| 2007/0280614 A1 | | 12/2007 | Karasawa | |
| 2008/0039693 A1 | | 2/2008 | Karasawa | |
| 2008/0058594 A1 | * | 3/2008 | Xie et al. | 600/109 |
| 2008/0221388 A1 | * | 9/2008 | Seibel et al. | 600/109 |
| 2010/0010302 A1 | * | 1/2010 | Hadani | 600/109 |
| 2010/0137684 A1 | * | 6/2010 | Shibasaki et al. | 600/109 |
| 2010/0268027 A1 | * | 10/2010 | Aono et al. | 600/109 |
| 2011/0054252 A1 | * | 3/2011 | Ozaki et al. | 600/109 |

FOREIGN PATENT DOCUMENTS

| | | | |
|---|---|---|---|
| JP | 2001-174744 | * | 6/2001 |
| JP | 3943927 | | 4/2007 |

* cited by examiner

*Primary Examiner* — Clayton E Laballe
*Assistant Examiner* — Kevin Butler
(74) *Attorney, Agent, or Firm* — Greenblum & Bernstein, P.L.C.

(57) ABSTRACT

A scanning endoscope apparatus, comprising a first transmitter, an actuator, a first optical filter, a second optical filter, a second transmitter, a first photo-detection unit, and a position determiner, is provided. The first transmitter transmits light to a first emission end. The actuator moves the first emission end. The first optical filter reflects the light of the first band. The second optical filter transmits the light of the first band at a transmittance that varies according to the position. The second transmitter transmits the light of the first band from a second incident end to a second emission end. The first photo-detection unit detects an amount of the light of the first band. The position determiner determines a position of the first emission end on the basis of the amount of the light of the first band.

23 Claims, 27 Drawing Sheets

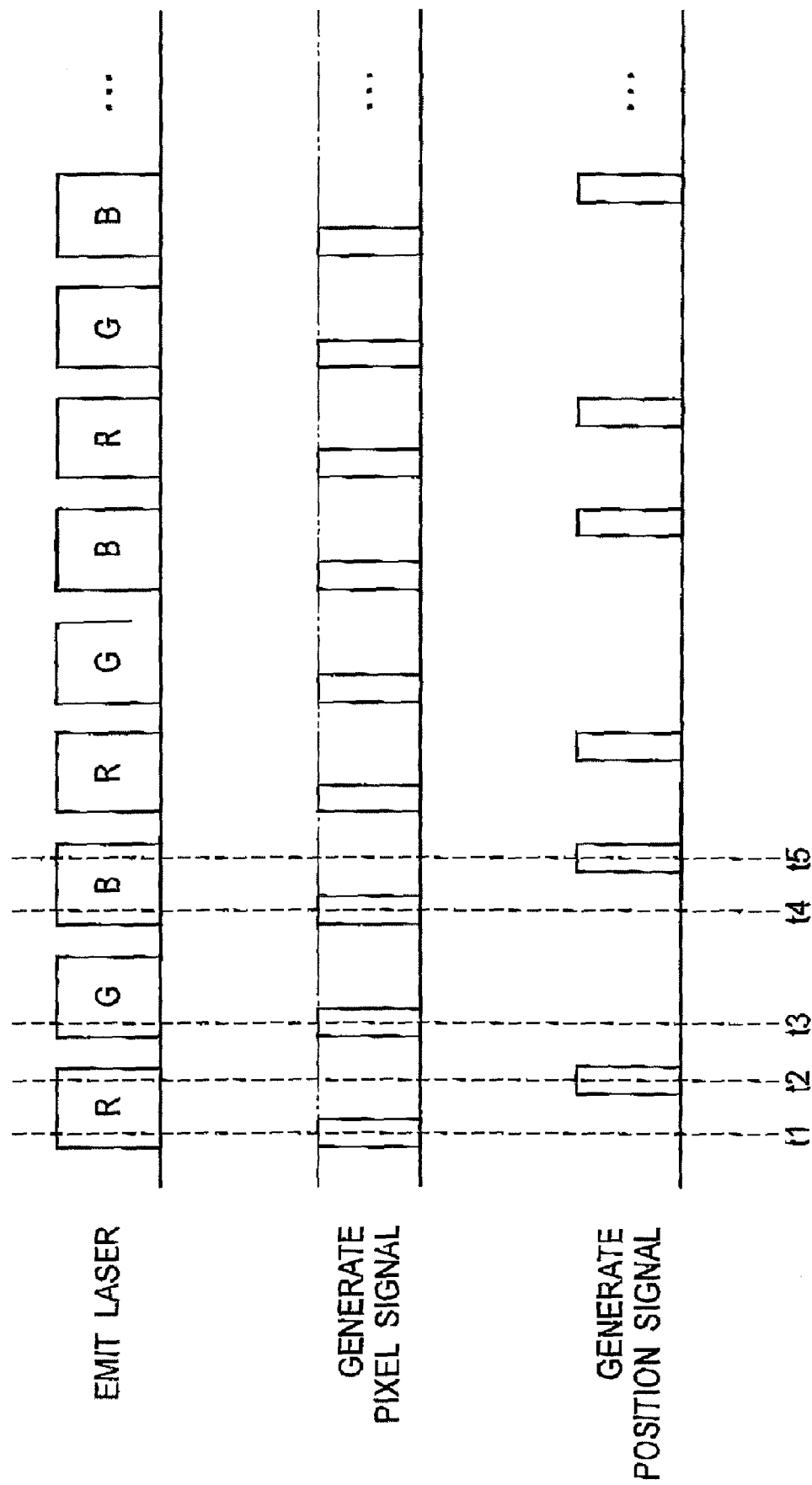

SCANNING ENDOSCOPE APPARATUS, SCANNING ENDOSCOPE, AND SCANNING ENDOSCOPE PROCESSOR

The present disclosure relates to subject matter contained in Japanese Patent Applications No. 2008-331814 (filed on Dec. 26, 2008) and No. 2008-331903 (filed on Dec. 26, 2008), which are expressly incorporated herein, by references, in their entireties.

BACKGROUND OF THE INVENTION

1. Field of the Invention

The present invention relates to a scanning endoscope apparatus that can detect the position of a moving emission end of a fiber that is part of a scanning endoscope.

2. Description of the Related Art

Japanese Patent No. 3943927 discloses a scanning endoscope. In a general scanning endoscope, light for illumination is transmitted through an optical fiber from a stationary incident end to a movable emission end and a scanning operation is carried out by successively moving the emission end of the optical fiber.

It is necessary to recognize a position of the emission end of the optical fiber in order to produce an accurate image. However, it is difficult to mount a position sensor in an insertion tuba that contains and supports the emission end of the fiber because the diameter of the insertion tube is ideally kept as thin as possible. Accordingly, the position of the moving emission end cannot be accurately detected, and its position is estimated on the basis of a driving signal for controlling the movement of the emission end. However, the image that is produced may be distorted if the accuracy of the estimation is low.

An accurate image can also be produced when the emission end is moved precisely along a predetermined course. However, when the position of the emission end happens to move away from the predetermined course, its off-course position cannot be detected, making it difficult to return the off-course position to the correct course.

SUMMARY OF THE INVENTION

Therefore, an object of the present invention is to provide a scanning endoscope apparatus that can detect the position of the emission end of the scanning endoscope.

According to the present invention, a scanning endoscope apparatus, comprising a first transmitter, an actuator, a first light source, a first optical filter, a second optical filter, a second transmitter, a first photo-detection unit, and a position determiner, is provided. The first transmitter transmits light received at a first incident end to a first emission end. The first transmitter emits a beam of the light exiting the first emission end. The actuator moves the first emission end in a direction perpendicular to an emission direction. The beam of the exiting light is emitted from the first emission end in the emission direction. The first light source unit emits light of a first band toward the first incident end. The first optical filter is mounted in the optical path of the light emitted from the first emission end. The first optical filter reflects the light of the first band. The first optical filter transmits light of a second band. The second band is outside of the first band. The second optical filter is mounted in the optical path of the light of the first band that is reflected by the first optical filter. The second optical filter transmits the light of the first band at a transmittance that varies according to the position on the second optical filter where the light of the first band makes contact. The second transmitter transmits the light of the first band, which passes through the second optical filter, from a second incident end to a second emission end. The first photo-detection unit detects an amount of the light of the first band that is emitted from the second emission end. The position determiner determines a position of the first emission and on the basis of the amount of the light of the first band that is detected by the first photo-detection unit.

According to the present invention, a scanning endoscope, comprising a first transmitter, an actuator, a first optical filter, a second optical filter, and a second transmitter, is provided. The first transmitter transmits light received at a first incident end to a first emission end. The first transmitter emits a beam of the light exiting the first emission end. The actuator moves the first emission end in a direction perpendicular to an emission direction. The beam of the exiting light is emitted from the first emission end in the emission direction. The first optical filter is mounted in the optical path of the light emitted from the first emission end. The first optical filter reflects the light of the first band. The first optical filter transmits light of a second band. The second band is outside of the first band. The second optical filter is mounted in the optical path of the light of the first band that is reflected by the first optical filter. The second optical filter transmits the light of the first band at a transmittance that varies according to the position on the second optical filter where the light of the first band makes contact. The second transmitter transmits the light of the first band, which passes through the second optical filter, from a second incident end to a second emission end.

According to the present invention, a scanning endoscope processor, comprising a first light source, a first photo-detection unit, and a position determiner, is provided. The scanning endoscope processor is connected with the scanning endoscope. The first light source unit emits light of a first band toward the first incident end. The first photo-detection unit detects an amount of the light of the first band that is emitted from the second emission end. The position determiner determines a position of the first emission end on the basis of the amount of the light of the first band that is detected by the first photo-detection unit.

According to the present invention, a scanning endoscope apparatus, comprising a light source, a first transmitter, an actuator, a third optical filter, a fourth optical filter, a second transmitter, and a third transmitter, is provided. The light source emits first light. The first transmitter transmits the first light emitted from the light source from a first incident end to a first emission end. The first transmitter emits a beam of the first light exiting the first emission end. The actuator moves the first emission end in a direction perpendicular to an emission direction. The beam of the exiting first light is emitted from the first emission end in the emission direction. The third optical filter is mounted in the optical path of the first light emitted from the first emission end. The third optical filter reflects a part of the first light. The third optical filter transmits a part of the first light. The fourth optical filter is mounted in the optical path of the first light reflected by the third optical filter. The fourth optical filter transmits the first light at a transmittance that varies according to the position on the fourth optical filter where the first light makes contact. The second transmitter transmits the first light, which passes through the fourth optical filter, from a second incident end to a second emission end. The third transmitter receives reflected light or fluorescence from an observation area that has been illuminated with the first light that passed through the third optical filter at a third incident end. The third transmitter transmits the reflected light or fluorescence from the third incident end to a third emission end. The pixel signal is generated for the observation area according to an amount of the first light or fluorescence that is emitted from the third emission end. The position of the first emission end is determined on the basis of an amount of the first light emitted from the second emission end.

According to the present invention, a scanning endoscope, comprising a first transmitter, an actuator, a third optical filter, a fourth optical filter, a second transmitter, and a third transmitter, is provided. The first transmitter transmits first light from a first incident end to a first emission end. The first transmitter emits a beam of the first light exiting from the first emission end. The actuator moves the first emission end in a direction perpendicular to an emission direction. The beam of the exiting first light is emitted from the first emission end in the emission direction. The third optical filter is mounted in the optical path of the first light emitted from the first emission end. The third optical filter reflects a part of the first light. The third optical filter transmits a part of the first light. The fourth optical filter is mounted in the optical path of the first light reflected by the third optical filter. The fourth optical filter transmits the first light at a transmittance that varies according to the position on the fourth optical filter where the first light makes contact. The second transmitter transmits the first light, which passes through the fourth optical filter, from a second incident end to a second emission end. The third transmitter receives reflected light or fluorescence from an observation area that has been illuminated with the first light that passes through the third optical filter at a third incident end. The third transmitter transmits the reflected light or fluorescence from the third incident end to a third emission end.

According to the present invention, a scanning endoscope processor, comprising a light source is provided. The scanning endoscope processor is connected to the scanning endoscope. The light source emits the first light toward the first incident end. The pixel signal is generated for the observation area according to an amount of the first light or fluorescence that is emitted from the third emission end. The position of the first emission end is determined on the basis of an amount of the first light emitted from the second emission end.

BRIEF DESCRIPTION OF THE DRAWINGS

The objects and advantages of the present invention will be better understood from the following description, with reference to the accompanying drawings in which:

FIG. 27 is a timing chart showing the operations of the light-source unit, the light-capturing unit, the first and second liquid crystal shutters, the image-processing unit, and the scanning drivers in the second embodiment.

DESCRIPTION OF THE PREFERRED EMBODIMENTS

Figure 1:
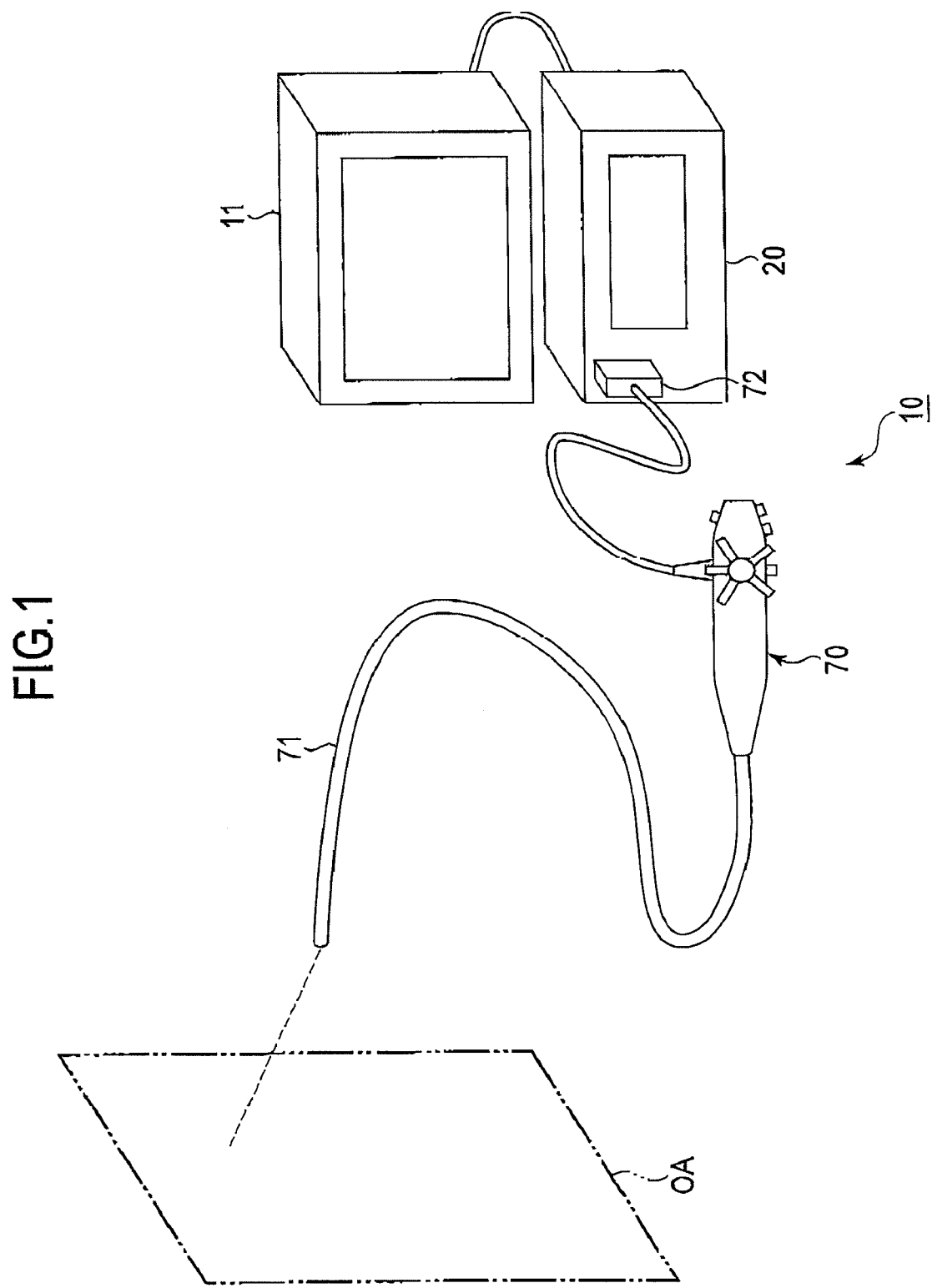
FIG. 1 is a schematic illustration of a scanning endoscope apparatus of the first embodiment of the present invention.

The present invention is described below with reference to the embodiments shown in the drawings.

In FIG. 1, the scanning endoscope apparatus 10 comprises a scanning endoscope processor 20, a scanning endoscope 70, and a monitor 11. The scanning endo scope processor 20 is connected to the scanning endoscope 70 and the monitor 11.

Hereinafter, an emission end of an illumination fiber (not depicted in FIG. 1), incident ends of image fibers (not depicted in FIG. 1), and an incident end of a position detection fiber (not depicted in FIG. 1) are ends mounted in the distal end of the insertion tube 71 of the scanning endoscope 70. In addition, an incident end of the illumination fiber (first incident end), emission ends of the image fibers (third emission end), and an emission end of the position detection fiber (second emission end) are ends mounted in a connector 72 that is connected to the scanning endoscope processor 20.

The scanning endoscope processor 20 provides light that is shined on an observation area (see "OA" in FIG. 1). The light emitted from the scanning endoscope processor 20 is transmitted to the distal end of the insertion tube 71 through the illumination fiber (first transmitter), and is shined toward a point on the observation area. Light reflected from the illuminated point is transmitted from the distal end of the insertion tube 71 to the scanning endoscope processor 20.

The direction of the emission end of the illumination fiber (first emission end) is changed by a fiber actuator (not depicted in FIG. 1). By changing the direction, the observation area is scanned with the light emitted from the illumination fiber. The fiber actuator is controlled by the scanning endoscope processor 20.

The scanning endoscope processor 20 receives reflected light which is scattered at the illuminated point, and generates a pixel signal according to the amount of received light. One frame of an image signal is generated by generating pixel signals corresponding to the illuminated points entirely dispersed in the observation area. The generated image signal is transmitted to the monitor 11, where an image corresponding to the received image signal is displayed.

Figure 2:
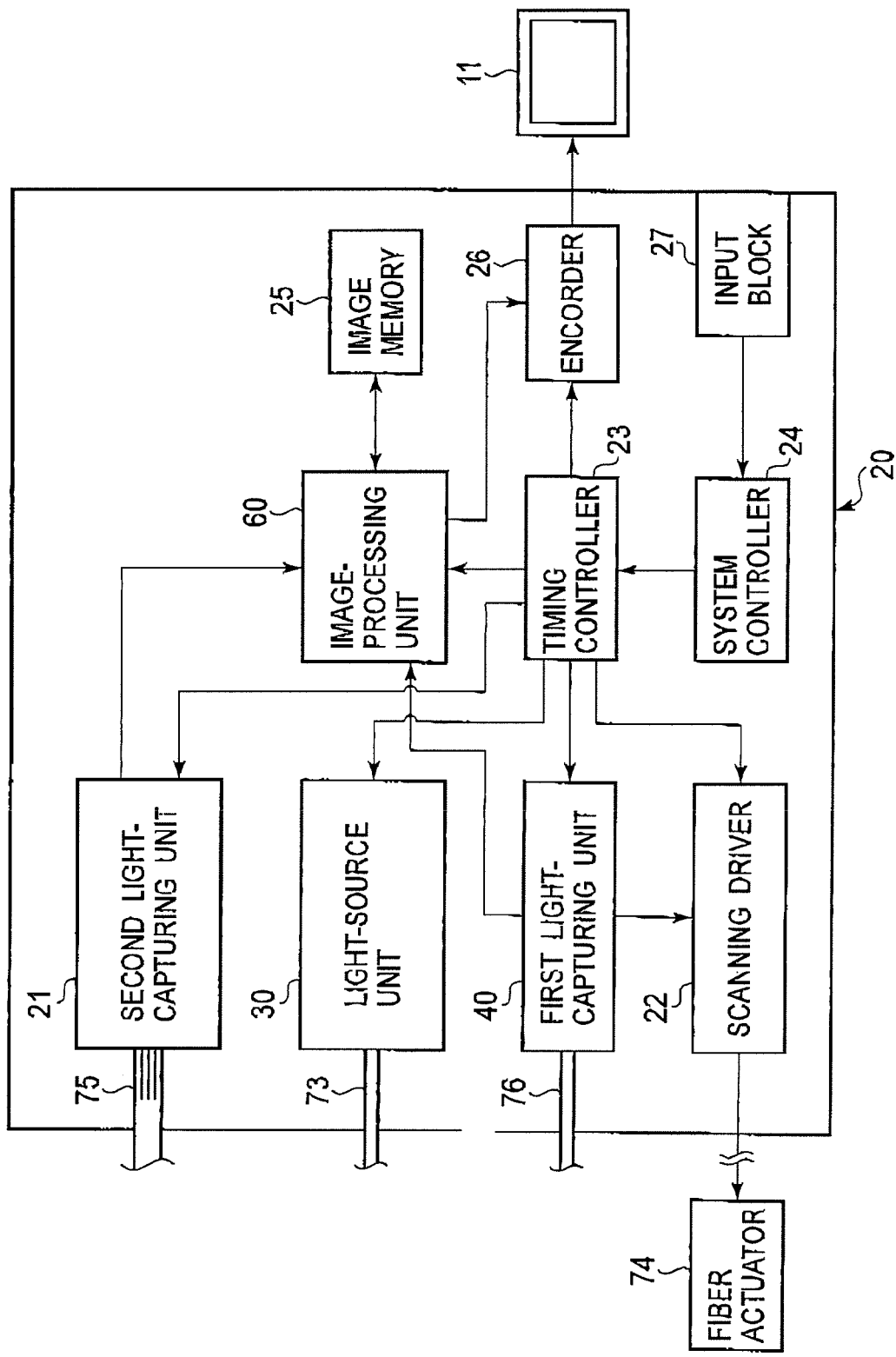
FIG. 2 is a block diagram schematically showing the internal structure of the scanning endoscope processor of the first embodiment.

As shown in FIG. 2, the scanning endoscope processor comprises a light-source unit 30, first and second light-capturing units 40 and 21 (first and second photo-detection units), a scanning driver 22 (scanning driver, corrector), an image-processing unit 60 (position determiner, image producer), a timing controller 23, a system controller 24, and other components.

As described later, light for illuminating an observation area and light for detecting the position of the moving emission end of the illumination fiber 73 are supplied from the light-source unit 30 to the illumination fiber 73. The scanning driver 22 controls the fiber actuator 74 to move the emission end of the illumination fiber 73.

The light reflected from the illuminated observation area is transmitted to the scanning endoscope processor 20 by the scanning endoscope 70. In addition, the light that reveals the position of the moving emission end of the illumination fiber 73 is also transmitted to the scanning endoscope processor 20. The reflected light and the light for detecting the position are made incident on the first and second light-capturing units 40 and 21, respectively.

The second light-capturing unit 21 generates a pixel signal according to the amount of reflected light. The first light-capturing unit 40 generates a position signal according to the position of the moving emission end of the illumination fiber 73. The pixel signal and the position signal are transmitted to the image-processing unit 60.

The image-processing unit 60 stores the received pixel signal at the address of the image memory 25 according to the position signal. Once pixel signals corresponding to the illuminated points dispersed throughout the observation area have been stored, the image-processing unit 60 carries out predetermined image processing on the pixel signals, and then one frame of the image signal is transmitted to the monitor 11 via the encoder 26.

By connecting the scanning endoscope 70 to the scanning endoscope processor 20, optical connections are made between the light-source unit 30 and the illumination fiber 73 mounted in the scanning endoscope 70, between the second light-capturing unit 21 and the image fibers 75 (third transmitter), and between the first light-capturing unit 40 and the position detection fiber 76 (second transmitter).

In addition, by connecting the scanning endoscope to the scanning endoscope processor 20, the fiber actuator 74 mounted in the scanning endoscope 70 is electrically connected with the scanning driver 22.

The timing for carrying out operations of the light-source unit 30, the first and second light-capturing units 40 and 21, the scanning driver 22, the image-processing unit 60, and the encoder 26 is controlled by the timing controller 23. In addition, the timing controller 23 and other components of the scanning endoscope apparatus 10 are controlled by the system controller 24. A user can input commands to the input block 27, which comprises a front panel (not depicted) and other mechanisms.

Figure 3:
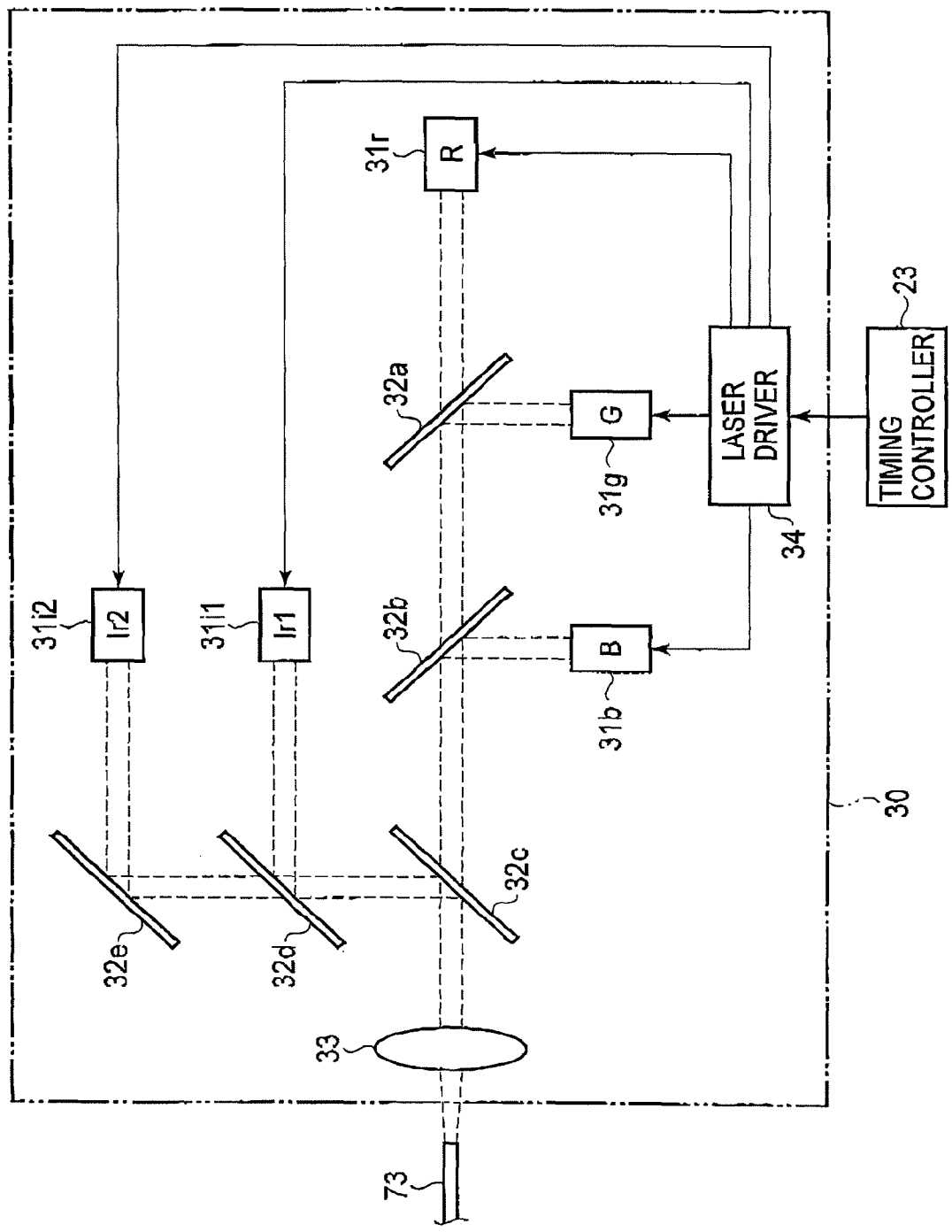
FIG. 3 is a block diagram schematically showing the internal structure of the light-source unit of the first embodiment.

As shown in FIG. 3, the light-source unit 30 comprises red, green, and blue lasers 31r, 31g, and 31b (second light source unit), a first infrared laser 31i1 (first light source unit, first light source), a second infrared laser 31i2 (first light source unit, second light source), first-fifth filters 32a-32e, a condenser lens 33, a laser driver 34, and other components.

The red, green, and blue lasers 31r, 31g, and 31b emit red, green, and blue laser beams, respectively. The first and second infrared lasers 31i1 and 31i2 emit first and second infrared laser beams (light of the first band), respectively. The wavelengths of the first and second laser beams range between the third and fourth bands, respectively. The third and fourth bands are within the band of infrared light (first band), which is outside of the band of visible light (second band), and the third and fourth bands do not overlap with each other.

The first filter 32a reflects the band of green light that the green laser 31g emits, and transmits the other bands. The second filter 32b reflects the band of blue light that the blue laser 31b emits, and transmits the other bands.

The third filter 32c reflects the third and fourth bands of infrared light, and transmits the other bands. The fourth filter 32d reflects the third band of infrared light, and transmits the other bands of infrared light. The fifth filter 32e is a mirror that reflects the fourth band of infrared light.

The first filter 32a, the second filter 32b, the third filter 32c, and the condenser lens 33, are arranged on the optical path of the red laser beam that is emitted from the red laser 31r toward the incident end of the illumination fiber 73, which is connected to the light-source unit 30. The first to third filters 32a, 32b and 32c are fixed so that their surfaces are inclined by 45 degrees against the optical path of the red laser beam.

The green laser 31g is arranged so that the green laser beam emitted by the green laser 31g is reflected by the first filter 32a, passes through the second and third filters 32b and 32c, and is made incident on the incident end of the illumination fiber 73.

The blue laser 31b is arranged so that the blue laser beam emitted by the blue laser 31b is reflected by the second filter 32b, passes through the third filter 32c, and is made incident on the incident end of the illumination fiber 73.

The fourth filter 32d and the first infrared laser 31i1 are arranged so that the first infrared laser beam emitted by the first infrared laser 31i1 is reflected by the fourth and third filters 32d and 32c, and is made incident on the incident end of the illumination fiber 73.

The fifth filter 32e and the second infrared laser 31i2 are arranged so that the second infrared laser beam emitted by the second infrared laser 31i2 is reflected by the fifth filter 32e, passes through the fourth filter 32d, is reflected by the third filter 32c, and is made incident on the incident end of the illumination fiber 73.

The first and second infrared, blue, green, and red laser beams are condensed by the condenser lens 33, and made incident on the incident end of the illumination fiber 73.

Upon observing a real-time image in the peripheral area around the distal end of the insertion tube 71, the red, green, and blue laser beams are mixed into a white laser beam, and the white laser beam and the first and second infrared laser beams are supplied to the illumination fiber 73.

The laser driver 34 drives the red, green, blue, first infrared, and second infrared lasers 31r, 31g, 31b, 31i1, and 31i2. In addition, on the basis of the control of the timing controller 23, the laser driver 34 controls the light-on and -off timing for the lasers 31r, 31g, 31b, 31i1, and 31i2.

Figure 4:
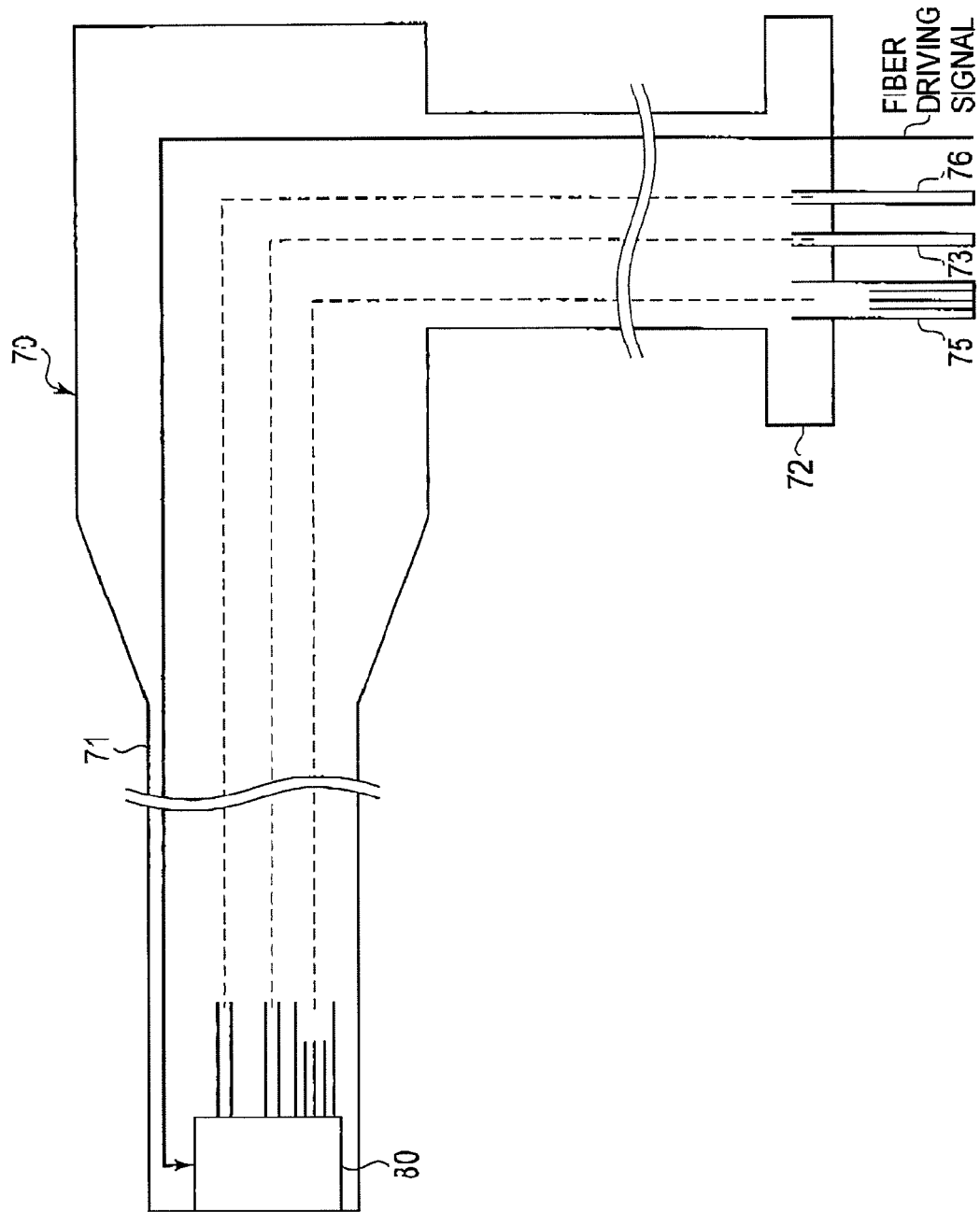
FIG. 4 is a block diagram schematically showing the internal structure of the scanning endoscope of the first embodiment.

Next, the structure of the scanning endoscope 70 is explained. As shown in FIG. 4, the scanning endoscope 70 comprises the illumination fiber 73, the image fibers 75, the position detection fiber 76, a head end unit 80, and other components.

The head end unit 80 is arranged on the distal end of the insertion tube 71. The illumination fiber 73, the image fibers 75, and the position detection fiber 76 are arranged inside the scanning endoscope 70 from the connector 72 to the head end unit 80.

Figure 5:
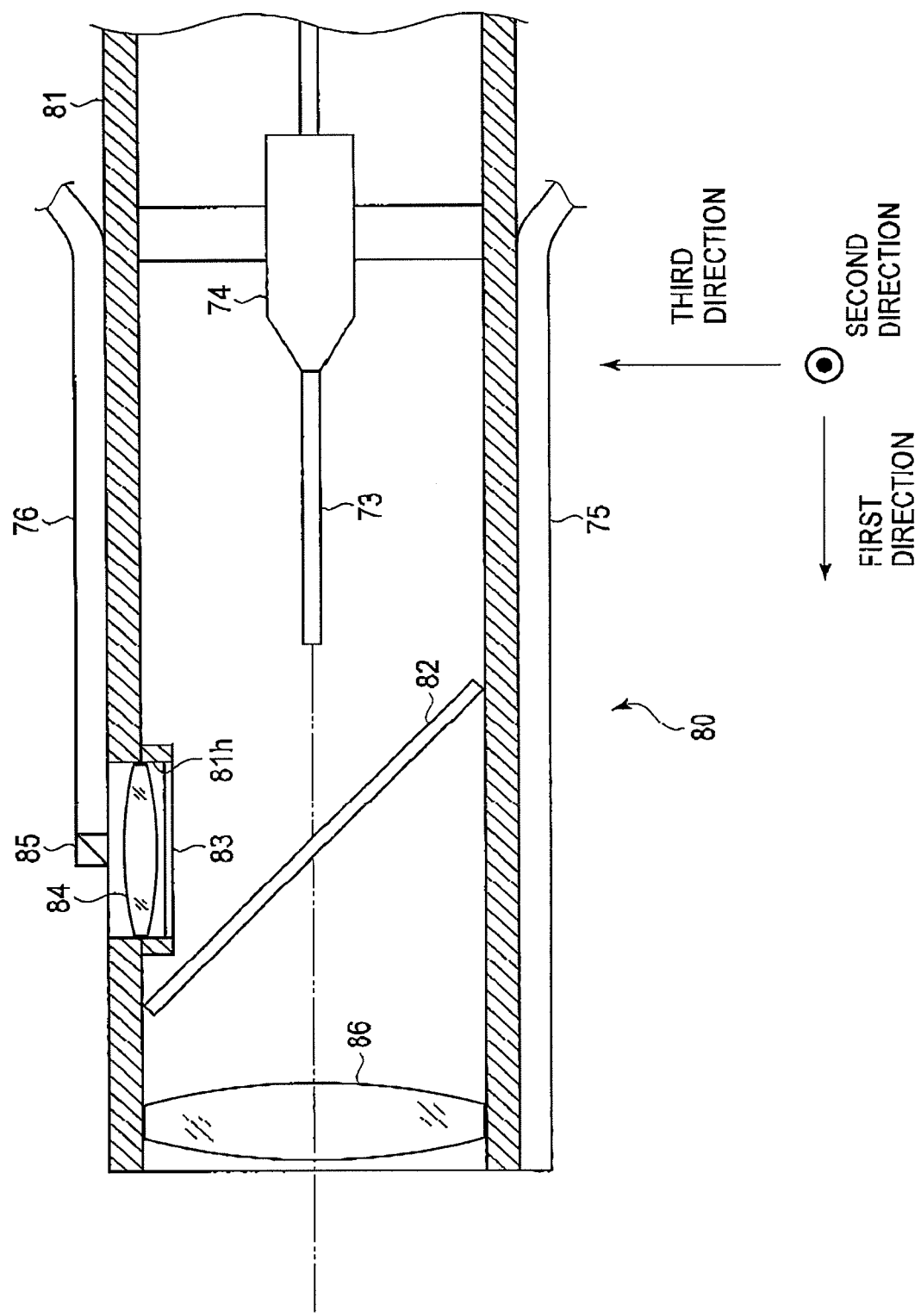
FIG. 5 is a structural diagram schematically showing the internal structure of the head end unit of the first embodiment.

As shown in FIG. 5, the head end unit 80 comprises a hollow tube 81, the fiber actuator 74, a beam splitter 82 (first optical filter), a position detection filter 83 (second optical filter), a condenser lens 84, a mirror 85, and a lens 86. The hollow tube 81 is made of solid material and shaped as a cylinder. The hollow tube 81 is mounted at the distal end of the insertion tube 71. The hollow tube 81 is positioned so that the axial directions of the distal end of the insertion tube 71 and the hollow tube 81 are parallel.

Hereinafter, the direction in which light is emitted from the emission end of the illumination fiber 73 when the axial directions of the illumination fiber 73 at the emission end and the hollow tube 81 are parallel is defined as a first direction. In addition, a certain direction perpendicular to the first direction is defined as a second direction (second and fourth directions).

The illumination fiber 73 is supported inside the hollow tube 81 by the fiber actuator 74. The illumination fiber 73 is positioned in the hollow tube 81 so that the axial direction of the insertion illumination fiber 73 at the emission end is parallel to the first direction when the insertion tube 71 is not deflected by the fiber actuator 74.

Figure 6:
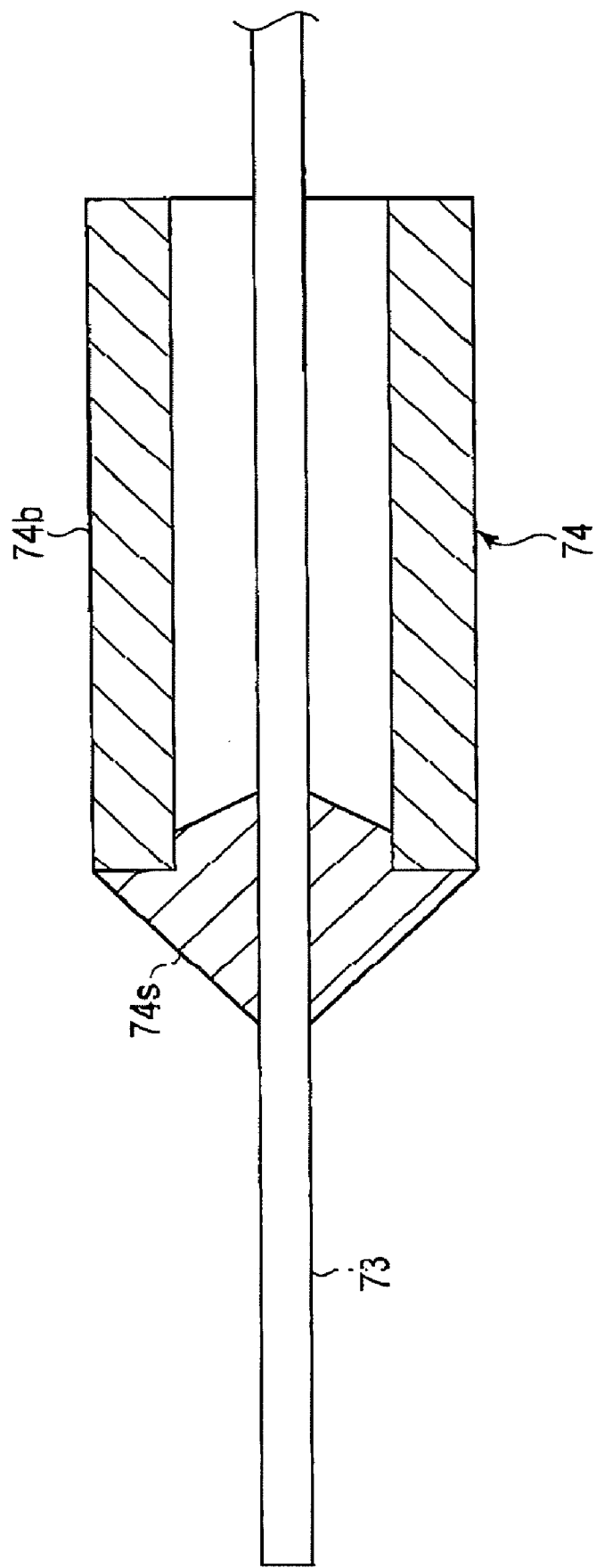
FIG. 6 is a sectional view of the fiber actuator along the axial direction of the illumination fiber for the purpose of illustrating the structure of the fiber actuator.

As shown in FIG. 6, the fiber actuator 74 comprises a supporting block 74s and a bending block 74b. The bending block 74b is shaped cylindrically. The illumination fiber 73 is inserted through the cylindrical bending block 74b. The illumination fiber 73 is supported at the forward end of the bending block 74b nearest the distal end of the insertion tube 71 by the supporting block 74s.

Figure 7:
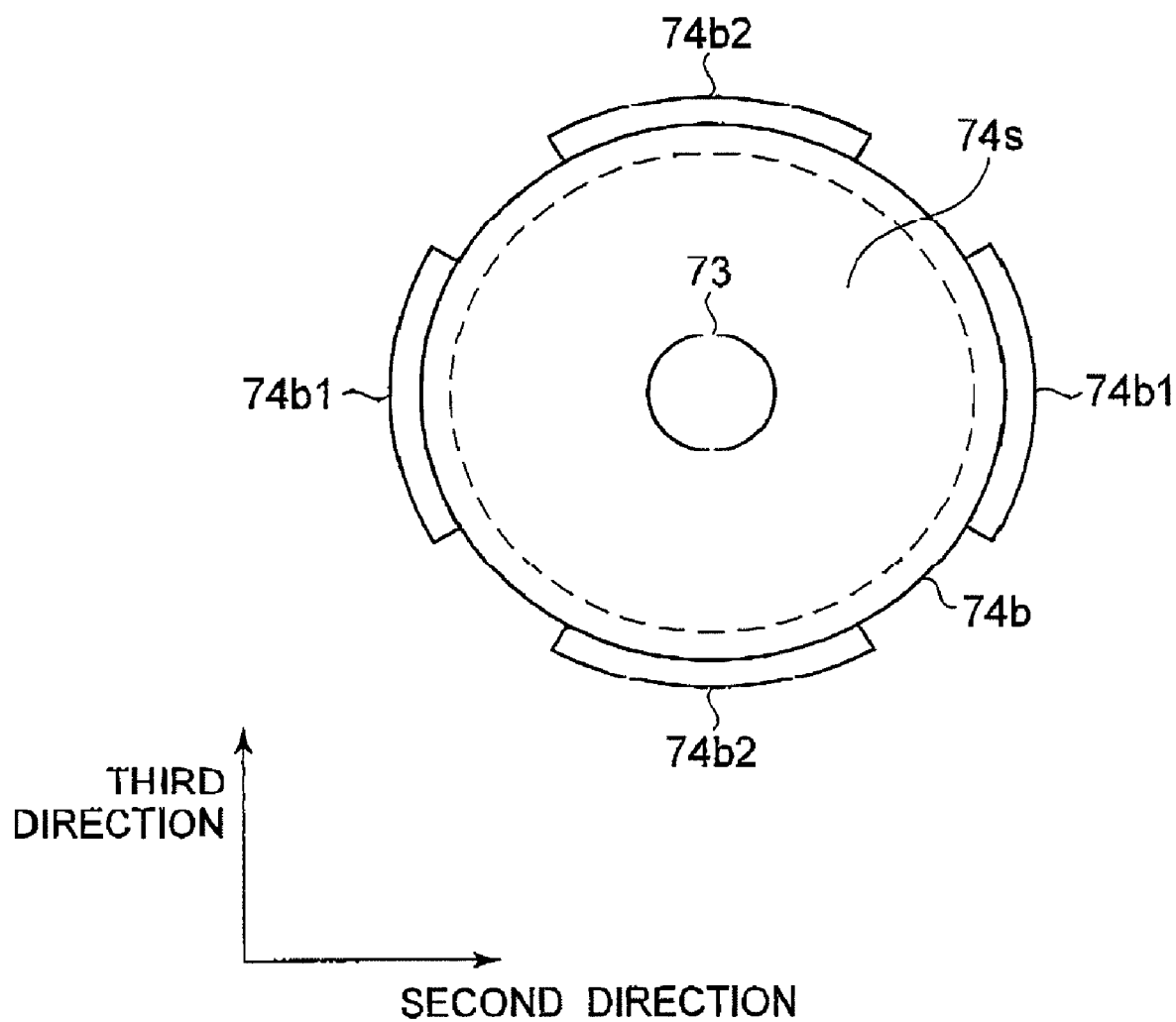
FIG. 7 is a front view of the fiber actuator as seen from the emission end of the illumination fiber.

As shown in FIG. 7, first and second bending elements 74b1 and 74b2 are fixed on the bending block 74b. The first and second bending elements 74b1 and 74b2 are pairs of two piezoelectric elements. In addition, the first and second bending elements 74b1 and 74b2 expand and contract along the axial direction of the cylindrical bending block 74b on the basis of a fiber driving signal transmitted from the scanning driver 22.

Two piezoelectric elements that constitute the first bending element 74b1 are fixed on the outside surface of the cylindrical bending block 74b in the second direction so that the axis of the cylindrical bending block 74b is between the piezoelectric elements. In addition, two piezoelectric elements that constitute the second bending element 74b2 are fixed on the outside surface of the cylindrical bending block 74b in a third direction so that the axis of the cylindrical bending block 74b is between the piezoelectric elements. The third direction is perpendicular to the first and second directions.

Figure 8:
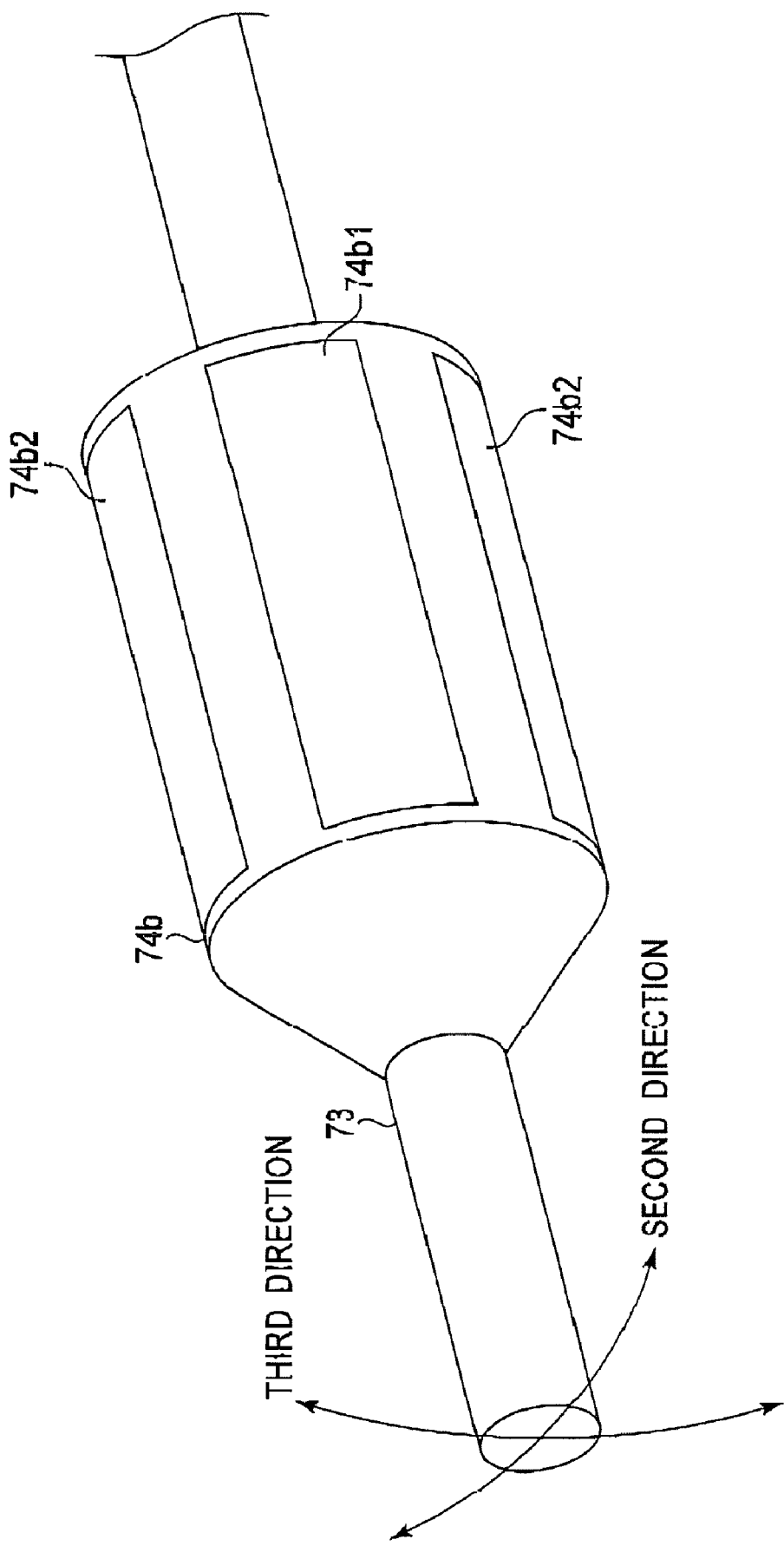
FIG. 8 is a perspective view of the fiber actuator.

As shown in FIG. 8, the bending block 74b bends along the second direction by expanding one of the piezoelectric elements that constitute the first bending element 74b1 and contracting the other at the same time. In addition, the bending block 74b bends along the third direction by expanding one of the piezoelectric elements that constitute the second bending element 74b2 and contracting the other at the same time.

The illumination fiber 73 is pushed in the second and/or third directions by the bending block 74b via the supporting block 74s, and the illumination fiber 73 bends toward the second and/or third directions, which are perpendicular to the direction in which light is emitted from the emission end of the illumination fiber 73 (emission direction). The emission end of the illumination fiber 73 is deflected by bending the illumination fiber 73.

Figure 9:
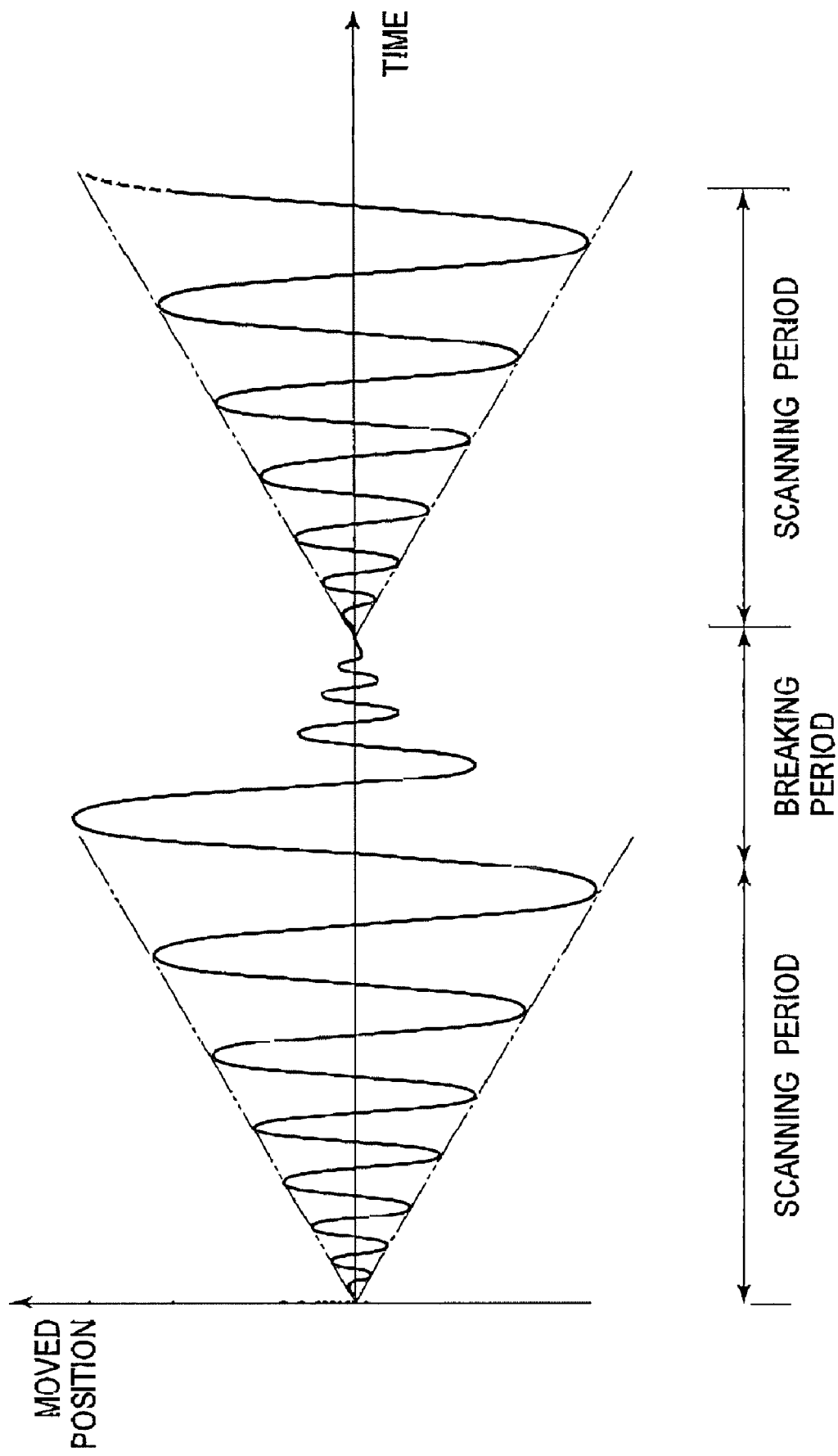
FIG. 9 is a graph illustrating the change in position of the emission end from the standard point in the second and third directions.

As shown in FIG. 9, the emission end of the illumination fiber 73 is moved so that the emission end vibrates along the second and third directions at amplitudes that are repetitively increased and decreased. The frequencies of the vibrations in the second and third directions are adjusted to be equal. In addition, the periods of increasing and decreasing amplitude of the vibration in the second and third directions are synchronized.

Figure 10:
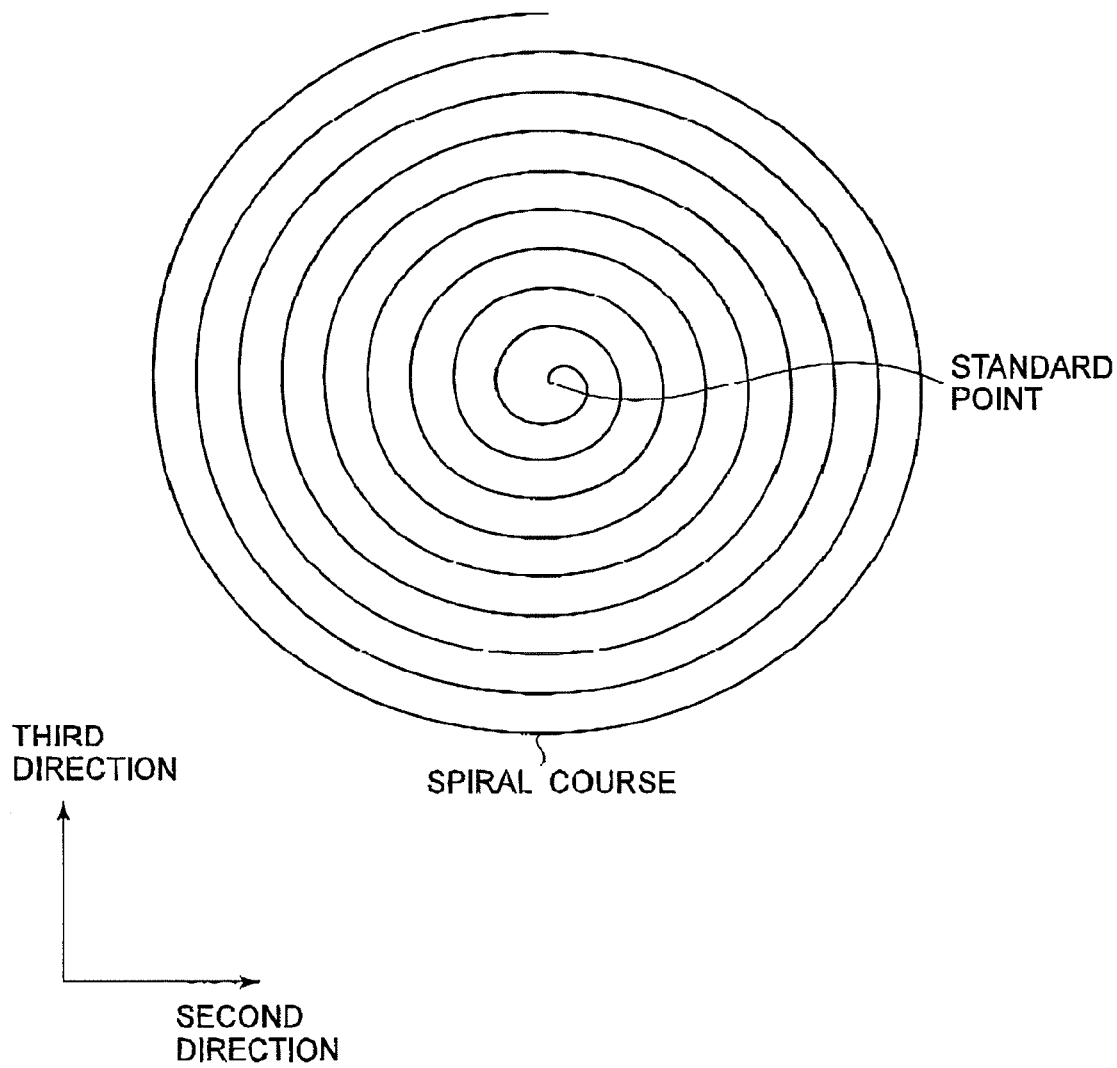
FIG. 10 is an illustration of a spiral course along which the emission end of the illumination fiber is moved by the fiber actuator.

By vibrating the emission end of the illumination fiber 73 in the second and third directions as described above, the emission end traces the spiral course shown in FIG. 10, and the observation area is scanned with light emitted from the emission end of the illumination fiber 73.

The position of the emission end of the illumination fiber 73 when it is not deflected is defined as a standard point. While the emission end is vibrated with increasing the amplitude starting from the standard point (see "scanning period" in FIG. 9), illumination of the observation area with the white laser beam and generation of pixel signals are carried out.

In addition, when the amplitude reaches a maximum level in the predetermined range, one scanning operation for producing one image terminates. After termination of a scanning operation, the emission end of the illumination fiber 73 is returned to the standard point by vibrating the emission end at decreasing amplitudes (see "braking period" in FIG. 9). When the emission end is returned to the standard point, it is the beginning of a scanning operation for generating another image.

The beam splitter 82 and the lens 86 are arranged in the direction in which light is emitted from the emission end of the illumination fiber 73 when the emission end is positioned at the standard point (see FIG. 5). The beam splitter 82 is shaped as a plate. The beam splitter 82 is fixed in the hollow tube 81 so that the surface of the beam splitter 82 is inclined by 45 degrees against the first direction. In addition, the lens 86 is fixed so that the optical axis of the lens 86 is parallel to the first direction.

The beam splitter 82 reflects the band of infrared light, and transmits the band of visible light. Accordingly, a white light component of the light emitted from the emission end of the illumination fiber 73 passes through the beam splitter 82. On the other hand, the first and second infrared light components, which are the same components as the first and second infrared laser beams, are reflected by the beam splitter 82 in the third direction.

An opening 81h is formed in the side of the hollow tube 81 where the infrared light components are reflected from the beam splitter 82. The position detection filter 83 and the condenser lens 84 are fixed inside of the opening 81h. The position detection filter 83 is shaped as a plate and positioned so that its surface is parallel to both the first and second directions. In addition, the condenser lens 84 is positioned so that the optical axis is parallel to the third direction.

Figure 11:
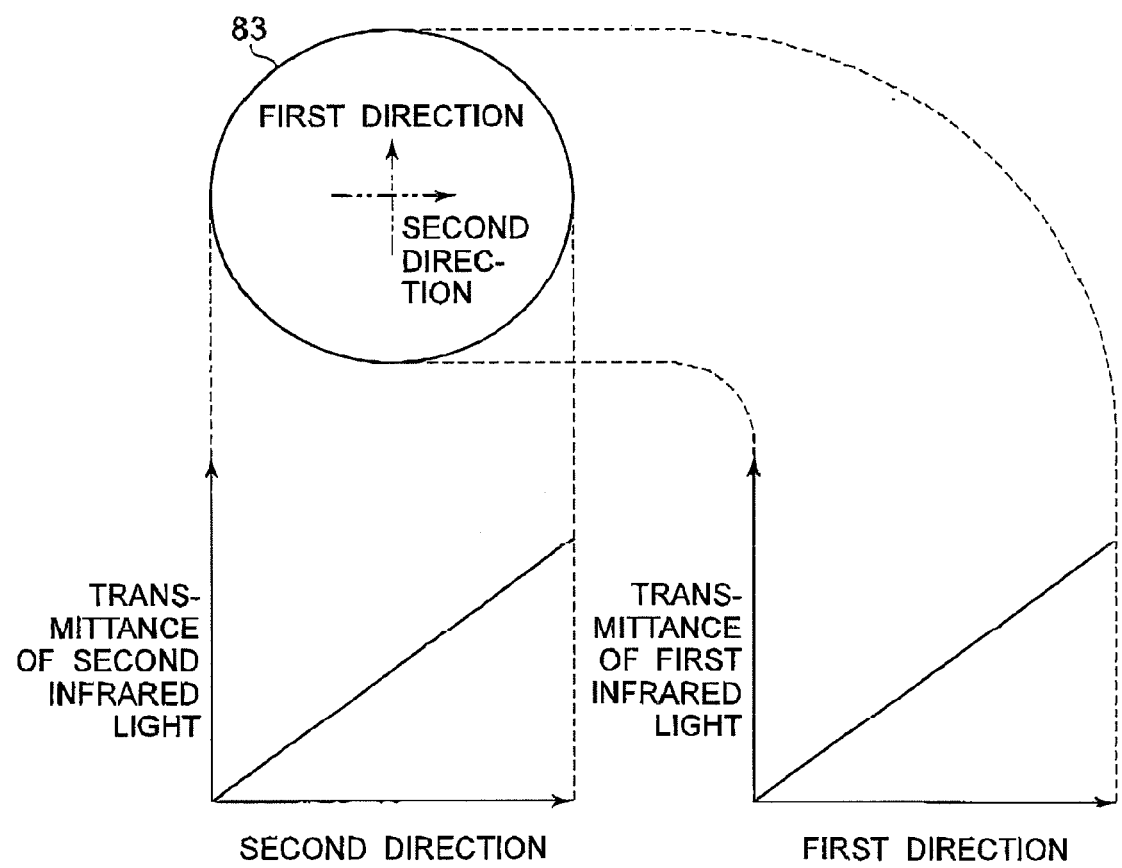
FIG. 11 is a graph illustrating the optical property of the position detection filter of the first embodiment.

The position detection filter 83 transmits the first and second infrared light components at varying transmittance levels according to the position of the position detection filter 83 on which light is incident. As shown in FIG. 11, the position detection filter 83 is formed so that the transmittance of the first infrared light component increases as the illuminated position of the position detection filter 83 moves toward the first direction. In addition, the position detection filter 83 is formed so that the transmittance of the second infrared light component increases as the illuminated position of the position detection filter 83 moves toward the second direction.

The infrared light components reflected by the beam splitter 82 pass through the position detection filter 83, and are condensed by the condenser lens 84. The mirror 85 is arranged so that the condensed infrared light components are reflected in the axial direction of the hollow tube 81 outside of the hollow tube 81.

The incident end of the position detection fiber 76 (second incident end) is arranged in the direction in which the infrared light components are reflected by the mirror 85. The infrared light components made incident on the position detection fiber 76 are transmitted to the first light-capturing unit 40 by the position detection fiber 76.

As described above, a white light component is also emitted from the emission end of the illumination fiber 73. The white light component passes through the beam splitter 82 and the lens 86, and is emitted toward one point within the observation area (see "OA" in FIG. 12). The reflected light is scattered at the point illuminated by the white light component. The scattered, reflected light is incident on the incident ends of the image fibers 75 (third incident end).

A plurality of the image fibers 75 are mounted in the scanning endoscope 70. The incident ends of the image fibers 75 are arranged around the lens 86. The light that is scattered and reflected from the illuminated point in the observation area is incident on all the image fibers 75.

The reflected light incident on the incident ends of the image fibers 75 is transmitted to the emission ends of the image fibers 75. As described above, the emission ends of the image fibers 75 are optically connected to the second light-capturing unit 21. The reflected light transmitted to the emission ends is incident on the second light-capturing unit 21.

Figure 13:
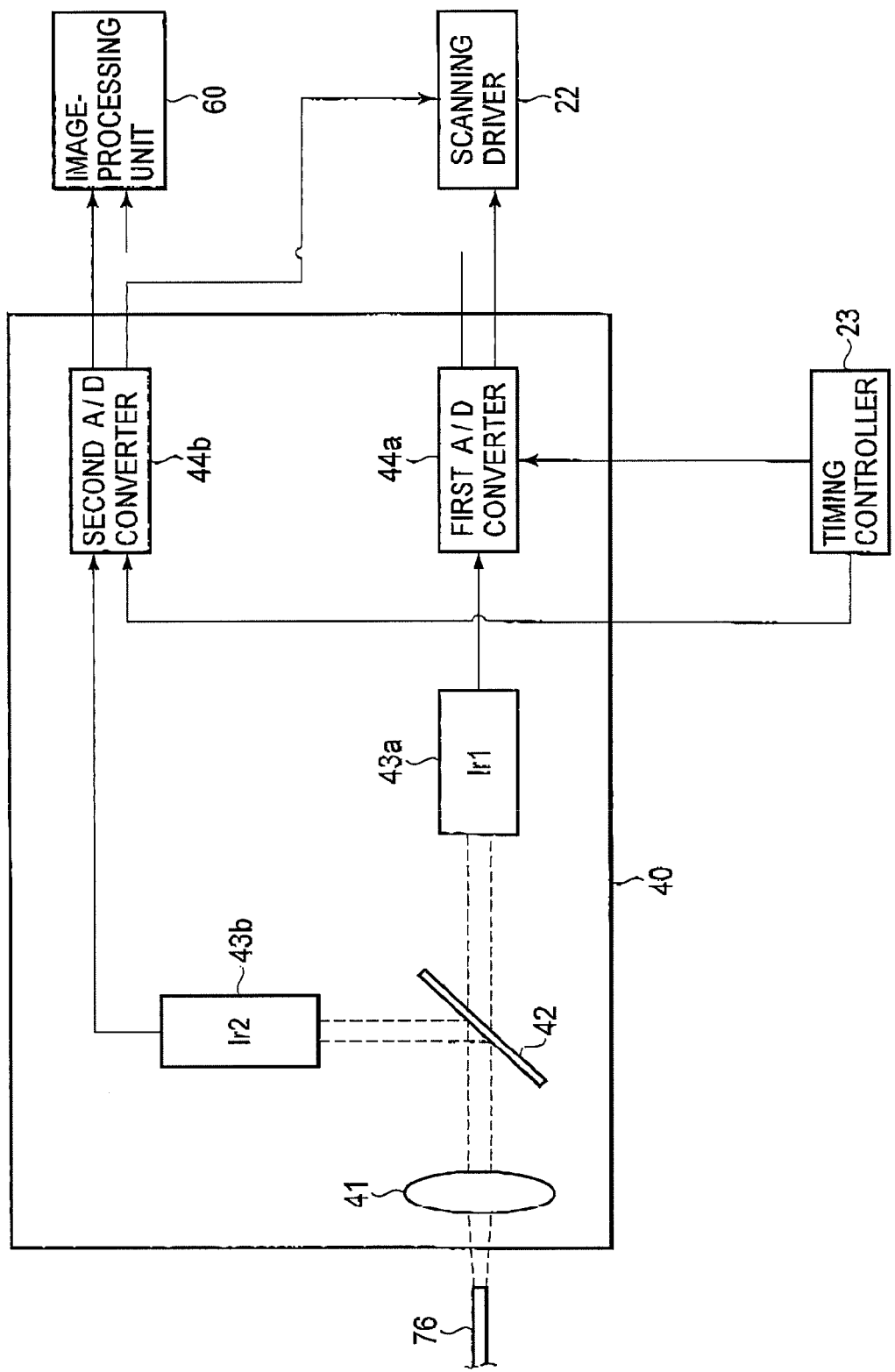
FIG. 13 is a block diagram schematically showing the internal structure of the first light-capturing unit of the first embodiment.

As shown in FIG. 13, the first light-capturing unit 40 comprises a collimating lens 41, a beam splitter 42, first and second photoelectric converters 43a and 43b (first and second detectors), and first and second A/D converters 44a and 44b.

The collimating lens 41, the beam splitter 42, and the first photoelectric converter 43a are arranged in a direction in which light is emitted from the emission end of the position detection fiber 76, which is connected to the first light-capturing unit 40.

The beam splitter 42 is fixed so that its surface is inclined by 45 degrees against the direction in which light is emitted from the emission end of the position detection fiber 76. The beam splitter 42 transmits the third band of infrared light, and reflects the fourth band of infrared light. The second photoelectric converter 43b is arranged in the direction in which the infrared light is reflected by the beam splitter 42.

The first and second infrared light components emitted from the emission end of the position detection fiber 76 reach the beam splitter 42 via the collimating lens 41. The first infrared light component passes through the beam splitter 42, and is made incident on the first photoelectric converter 43a.

The second infrared light component is reflected by the beam splitter 42, and is made incident on the second photoelectric converter 43b.

The first and second photoelectric converters 43a and 43b are photomultiplier tubes that generate electric signals according to the amount of light received. The first photoelectric converter 43a generates a first position signal according to the amount of the first infrared light component received. The second photoelectric converter 43b generates a second position signal according to the amount of the second infrared light component received. The generated first and second position signals are transmitted to the image-processing unit 60.

The second light-capturing unit 21 receives the reflected light from the image fiber 75. The second light-capturing unit 21 generates pixel signal components according to the amounts of red, green, and blue light components in the reflected light. The pixel signal components are transmitted to the image-processing unit 60.

The image-processing unit 60 determines the position of the point illuminated with the white light component on the basis of the first and second position signals. The image-processing unit 60 stores the received pixel signal components at the address of the image memory 25 that corresponds to the determined position.

As described above, the observation area is scanned with the white laser beam, pixel signals are generated on the basis of the reflected light at the respective points illuminated with the white laser beam, and the generated pixel signals are stored at the address corresponding to the points. The image signal corresponding to the observation area comprises the pixel signals corresponding to the points from the standard point to the scan-end point. As described above, the image-processing unit 60 carries out predetermined image processing on the image signal. After undergoing predetermined image processing, the image signal is transmitted to the monitor 11.

Figure 14:
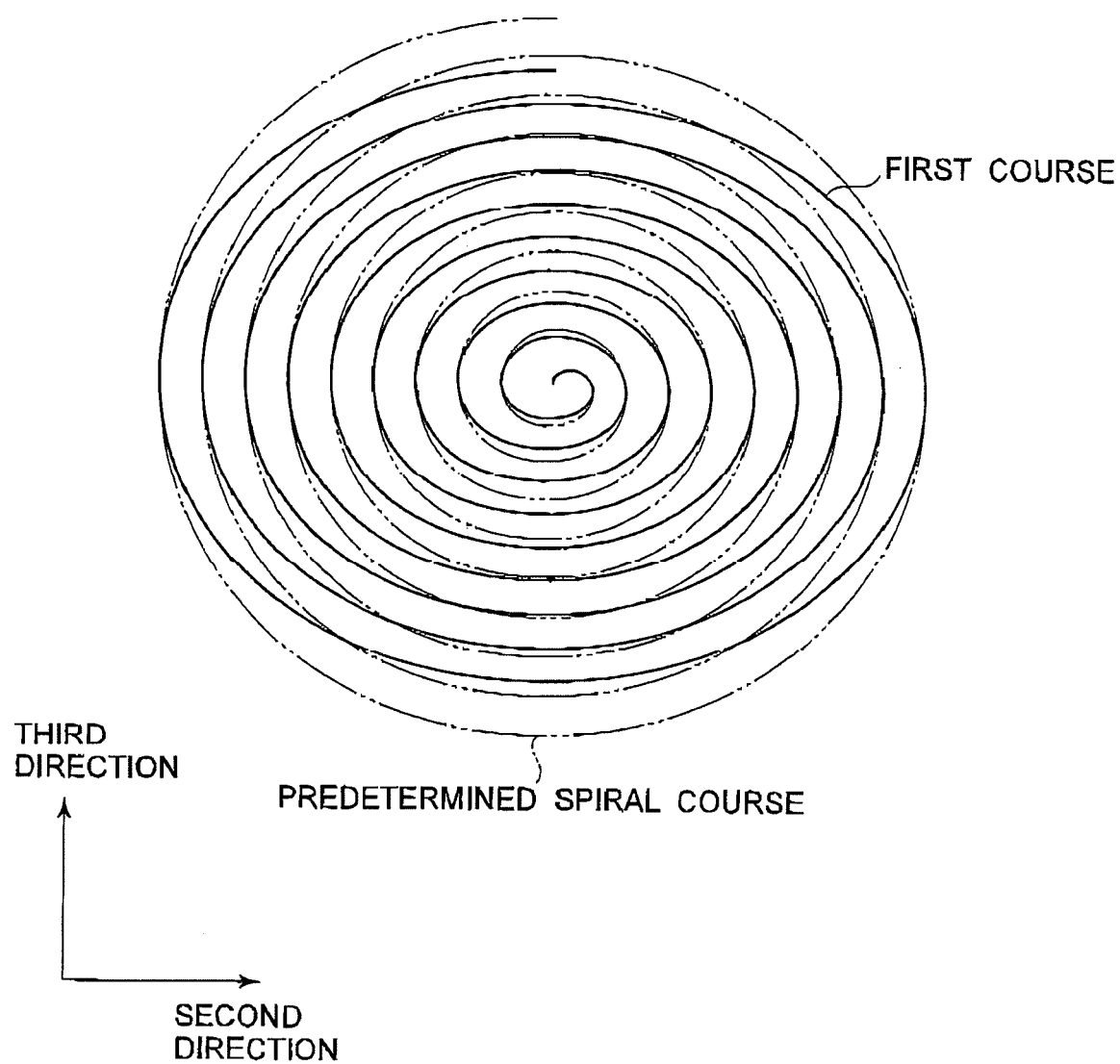
FIG. 14 is an illustration of a first course that coincides with a scaled down spiral course in the third direction.

It is necessary for the emission end of the illumination fiber 73 to trace the predetermined spiral course precisely in order to produce an accurate image. However, the moving emission end may be off of the spiral course due to various factors, such as a temperature variation or vibration around the fiber actuator 74. For example, if the emission end does not move sufficiently far enough in the third direction, the emission end will trace a first course (see solid line in FIG. 14) that coincides with the predetermined spiral course (see double dot and dash line) but is slightly compressed in the third direction.

When the next frame of an image signal is generated after generating one frame of an image signal, the image-processing unit 60 updates the pixel signal by storing the received pixel signal at the corresponding address if the determined position of the illuminated point is on the predetermined spiral course. Accordingly, pixel signals corresponding to pixels positioned at the points where the predetermined spiral course and the first course overlap with each other are updated.

On the other hand, the received pixel signal is deleted if the determined position of the illuminated point is off of the predetermined spiral course. Accordingly, pixel signals corresponding to pixels positioned at the points where the predetermined spiral course and the first course do not overlap are deleted without updating.

As in the above manner, if the emission end of the illumination fiber 73 does not trace the predetermined spiral course, a portion of the pixel signals stored in corresponding addresses are not updated. The pixel signals that are not updated, which are the same pixel signals from the previous frame, and the updated pixel signals constitute a new frame of an image signal.

If the emission end of the illumination fiber 73 continuously traces the first course, a portion of pixel signals will continue to not be updated. Consequently, an accurate real-time image cannot be displayed in this situation.

In order to resolve the above problem, the first and second position signals are also transmitted to the scanning driver 22. The scanning driver 22 determines on the basis of the successively received first and second position signals whether or not the emission end of the illumination fiber 73 is off of the predetermined spiral course. If the emission end is off of the spiral course, the scanning driver 22 generates the fiber driving signal, which is an adjustment to make the emission end return to the spiral course, and transmits the adjusted fiber driving signal to the fiber actuator 74.

In the first embodiment, the position of the emission end of the illumination fiber 73 can be determined. Because an image is produced by storing a pixel signal at an address corresponding to the determined position, the amount of distortion in an entire image can be reduced.

In addition, in the first embodiment, if the emission end of the illumination fiber 73 is off of the predetermined spiral course, the distortion of a produced image is prevented by updating only pixel signals stored in the addresses that correspond to the positions determined on the predetermined spiral course from a previous frame of the pixel signals.

In addition, in the first embodiment, if the emission end of the illumination fiber 73 is off of the predetermined spiral course, all or most of the pixel signals can be updated by adjusting the movement of the emission end of the illumination fiber 73 to trace the predetermined spiral course on the basis of the gap between the point of the spiral course and the actual position. Accordingly, an accurate real-time image can be reproduced.

Next, a scanning endoscope apparatus of the second embodiment is explained. The primary differences between the second embodiment and the first embodiment are the type of light emitted from the light-source unit and the operation of the light-source unit and light-capturing unit. The second embodiment is explained mainly with reference to the structures that differ from those of the first embodiment. Here, the same index numbers are used for the structures that correspond to those of the first embodiment.

Figure 15:
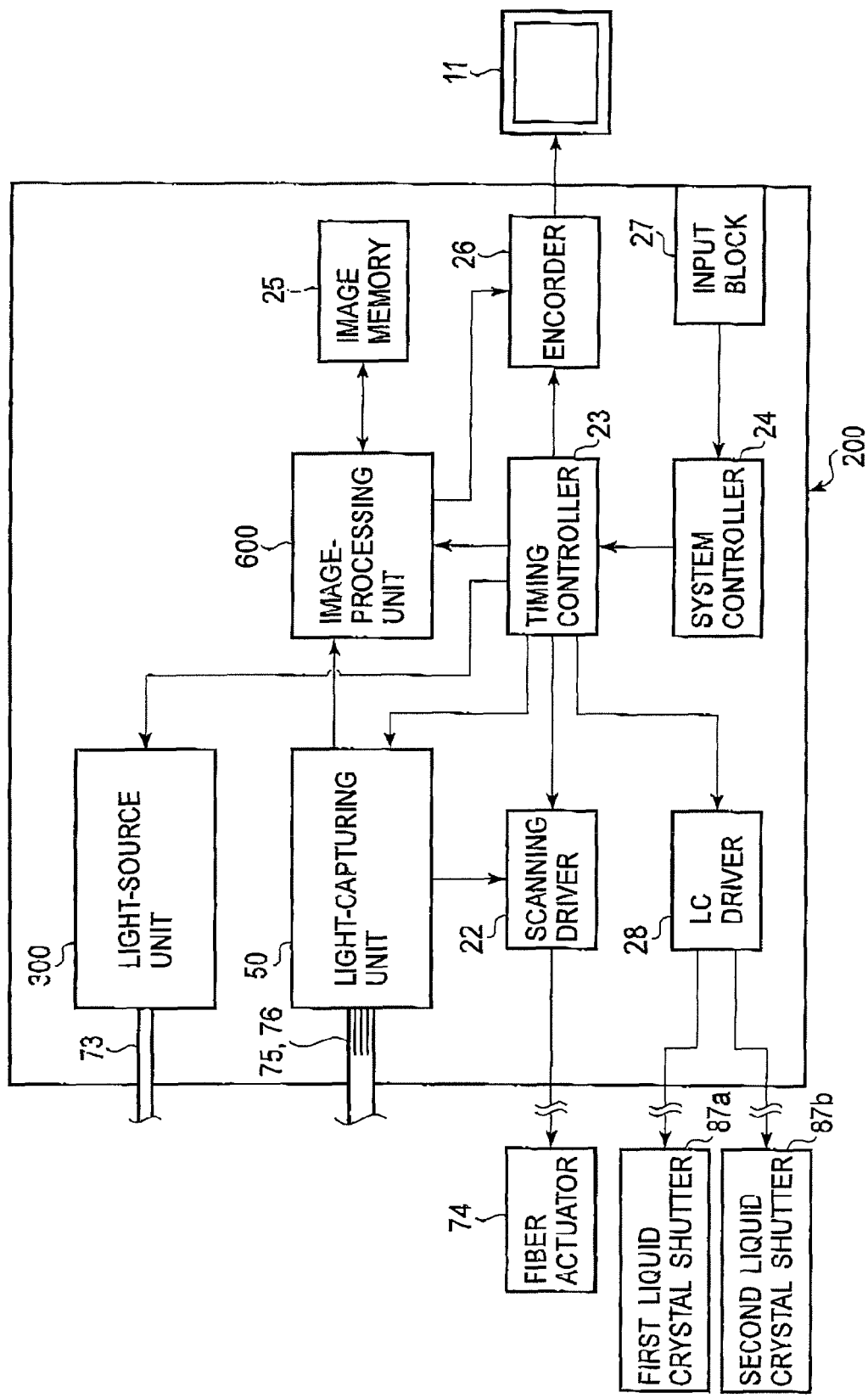
FIG. 15 is a block diagram schematically showing the internal structure of the scanning endoscope processor of the second embodiment.

As shown in FIG. 15, the scanning endoscope processor 200 comprises a light-source unit 300 (light source), an image-processing unit 600, a scanning driver 22 (scanning driver, corrector, position detector), a timing controller 23 (controller), a system controller 24, and other components, as in the first embodiment. The scanning endoscope processor comprises a light-capturing unit 50 (third photo-detection unit) and an LC driver 28, unlike in the first embodiment.

As in the first embodiment, light for illuminating an observation area and light for detecting the position of the moving emission end of the illumination fiber 73 are supplied from the light-source unit 300 to the illumination fiber 73. The LC driver 28 controls first and second liquid crystal shutters to alternate between transmitting and blocking light. The scanning driver 22 controls the fiber actuator 74 to move the emission end of the illumination fiber 73.

The light reflected from the illuminated observation area is transmitted to the scanning endoscope processor 200 by the scanning endoscope 700, as in the first embodiment. In addition, the light that reveals the position of the moving emission end of the illumination fiber 73 is also transmitted to the scanning endoscope processor 200, as in the first embodiment. The reflected light and the light for detecting the position are made incident on the light-capturing unit 50, unlike in the first embodiment.

The light-capturing unit 50 generates a light-quantity signal according to the amount of light received. The light-quantity signal is transmitted as a pixel signal to the image-processing unit 600. In addition, the light-quantity signal is transmitted as a position signal to the scanning driver 22.

The image-processing unit 600 receives a position control signal, which is transmitted from the timing controller 23 to the scanning driver 22. The position control signal is used for controlling the position of the emission end of the illumination fiber 73. The image-processing unit 600 stores the received pixel signal at the address of the image memory 25 according to the position control signal. Once pixel signals corresponding to the illuminated points dispersed throughout the observation area have been stored, the image-processing unit 600 carries out predetermined image processing on the pixel signals, and then one frame of the image signal is transmitted to the monitor 11 via the encoder 26, as in the first embodiment.

As in the first embodiment, the scanning driver 22 determines the course which the emission end actually traces on the basis of the position signal. If the emission end is off of the predetermined spiral course, the scanning driver 22 controls the fiber actuator 74 to make an adjustment so that the course being traced by the emission end returns to the predetermined spiral course.

By connecting the scanning endoscope 700 to the scanning endoscope processor 200, optical connections are made between the light-source unit 300 and the illumination fiber 73, and between the light-capturing unit 50 and the image and position detection fibers 75 and 76, unlike in the first embodiment.

In addition, by connecting the scanning endoscope 700 to the scanning endoscope processor 200, the fiber actuator 74 is electrically connected with the scanning driver 22, as in the first embodiment.

The functions of the timing controller 23, the system controller 24, and the input block 27 are the same as those in the first embodiment.

Figure 16:
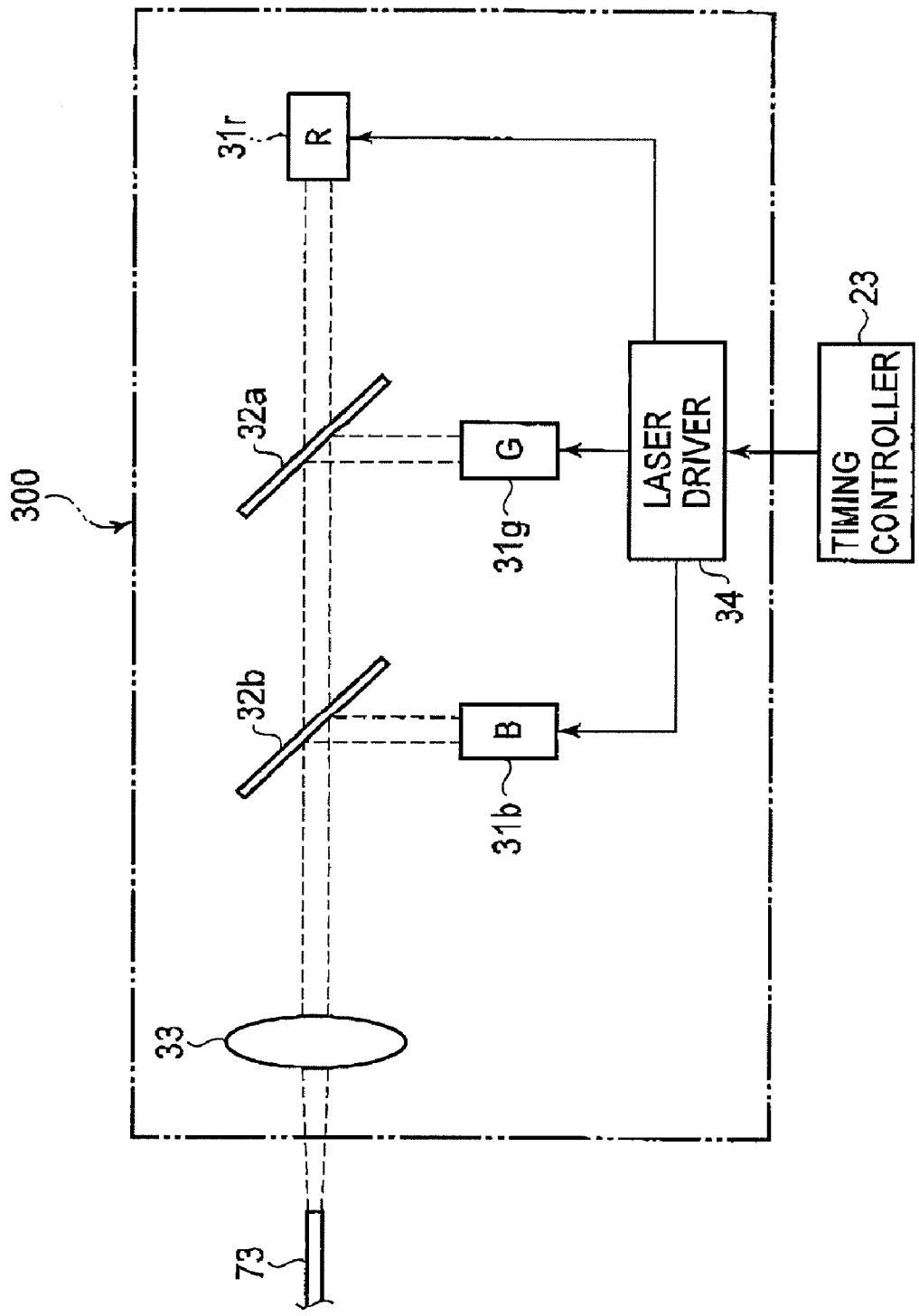
FIG. 16 is a block diagram schematically showing the internal structure of the light-source unit of the second and third embodiments.

As shown in FIG. 16, the light-source unit 300 comprises red, green, and blue lasers 31r, 31g, and 31b, first and second filters 32a and 32b, a condenser lens 33, a laser driver 34, and other components, as in the first embodiment. However, the light-source unit 300 does not comprise an infrared laser and third to fifth filters, unlike in the first embodiment.

The functions and the arrangements of the red, green, and blue lasers 31r, 31g, and 31b are the same as those of the first embodiment.

The functions and the arrangements of the first and second filters are the same as those of the first embodiment.

The red laser beam (second light), green laser beam (fourth light), and blue laser beam (third light) emitted from the red, green, and blue laser 31r, 31g, and 31b, respectively, are condensed by the condenser lens 33 and made incident on the incident end of the illumination fiber 73, as in the first embodiment.

Upon observing a real-time image in the peripheral area around the distal end of the insertion tube 71, each of the red, green, and blue laser beams are supplied to the illumination fiber 73 at separate points in time. The timing of emission for each laser beam (i.e., when each laser beam is made incident on the illumination fiber 73) is described later.

The laser driver 34 drives the red, green, and blue lasers 31r, 31g, and 31b, and controls the light-on and -off timing, as in the first embodiment.

Figure 17:
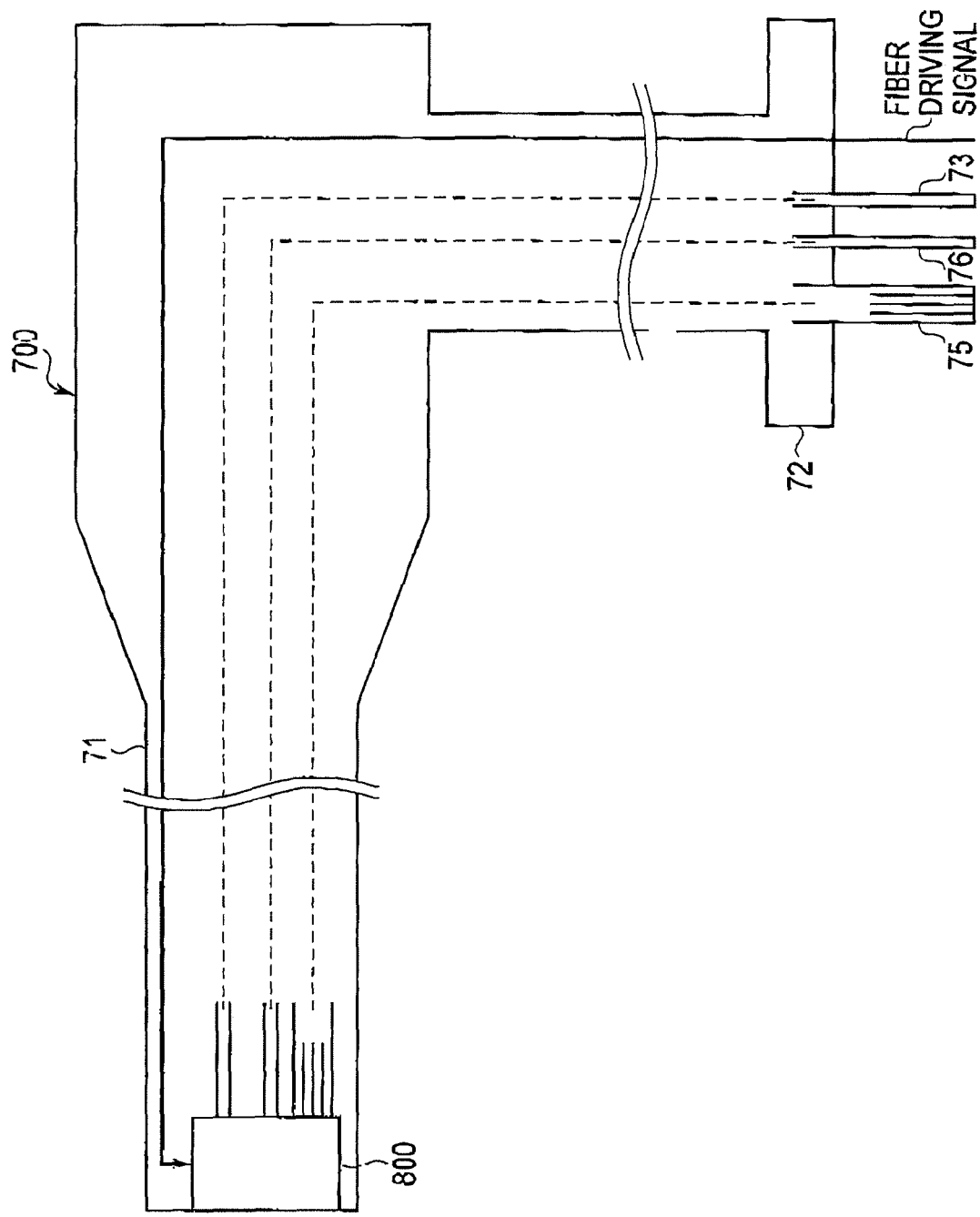
FIG. 17 is a block diagram schematically showing the internal structure of the scanning endoscope of the second embodiment.

Next, the structure of the scanning endoscope 700 is explained. As shown in FIG. 17, the scanning endoscope 700 comprises the illumination fiber 73, the image fibers 75, the position detection fiber 76, a head end unit 800, and other components, as in the first embodiment.

The arrangements of the head end unit 800, the illumination fiber 73, the image fibers 75, and the position detection fiber 76 in the scanning endoscope 700 are the same as those in the first embodiment.

Figure 18:
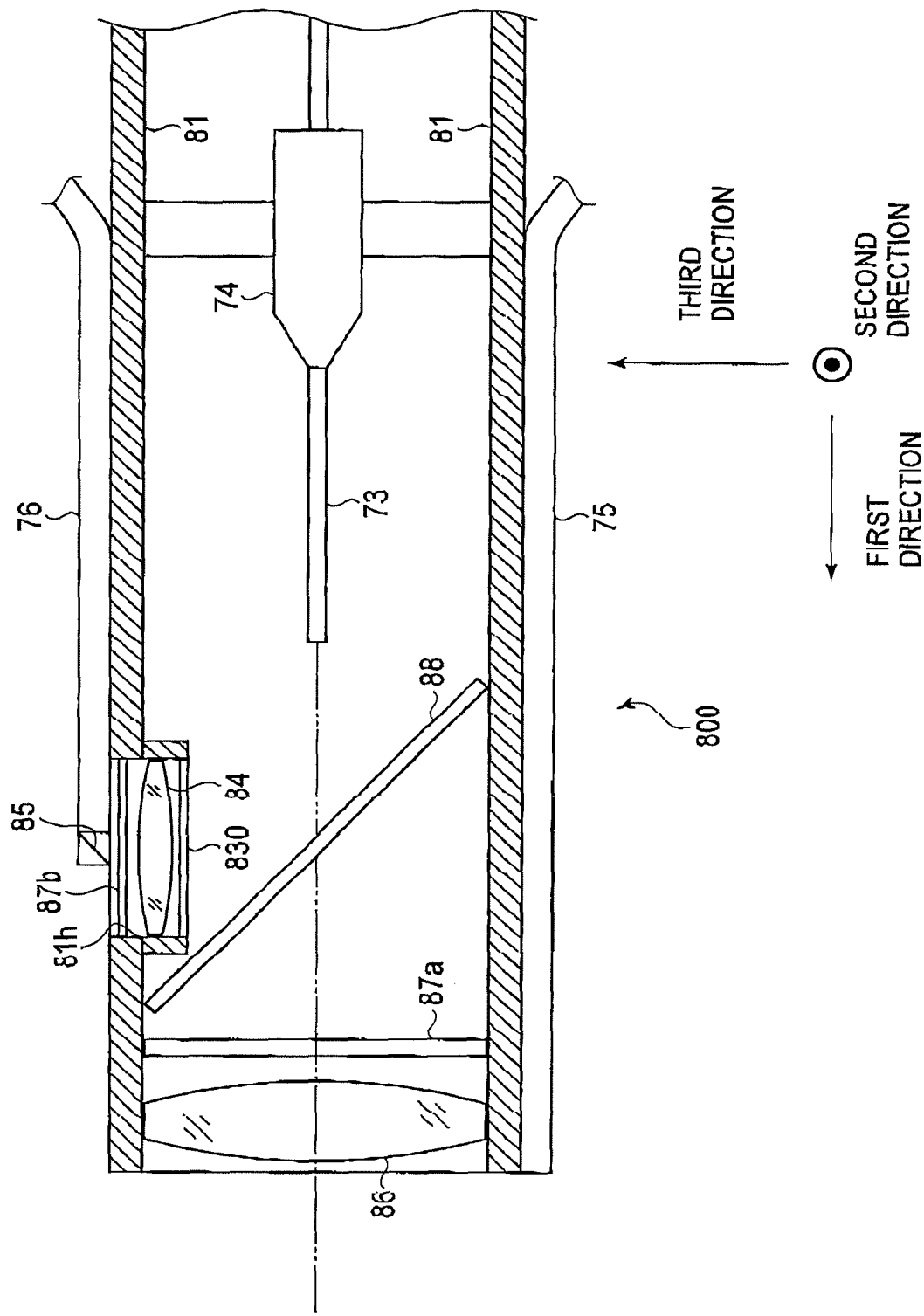
FIG. 18 is a structural diagram showing a cut-away view of the internal structure of the head end unit of the second embodiment.

As shown in FIG. 18, the head end unit 800 comprises a hollow tube 81, the fiber actuator 74, a position detection filter 830 (fourth optical filter), a condenser lens 84, a mirror 85, and a lens 86, as in the first embodiment. In addition, the head end unit 800 comprises the first and second liquid crystal shutters 87a and 87b (first and second shutters), and a half mirror 88 (third optical filter).

The structure, shape, and position of the hollow tube 81 are the same as in the first embodiment.

The definitions of the first, second, and third directions are the same as those in the first embodiment.

The illumination fiber 73 is supported inside the hollow tube 81 by the fiber actuator 74, as in the first embodiment. The position of the illumination fiber 73 at the emission end is the same as in the first embodiment.

The structure and function of the fiber actuator 74 are the same as in the first embodiment. Accordingly, the fiber actuator 74 makes the illumination fiber 73 bend toward the second and/or third directions. The emission end of the illumination fiber 73 is moved by bending the illumination fiber 73.

The emission end of the illumination fiber 73 is moved in the second and third directions, as in the first embodiment. Accordingly, the emission end traces the predetermined spiral course, and the observation area is scanned with the light emitted from the emission end.

The definition of the standard point is the same as that in the first embodiment. In addition, the period of the scanning operation and the period of termination of the scanning operation are the same as in the first embodiment.

The half mirror 88, the first liquid crystal shutter 87a, and the lens 86 are arranged in the direction in which light is emitted from the emission end of the illumination fiber 73 when the emission end is positioned at the standard point (see FIG. 18). The half mirror 88 is shaped as a plate. The half mirror 88 is fixed in the hollow tube 81 so that the surface of the half mirror 88 is inclined by 45 degree against the first direction. The first liquid crystal shutter 87a is fixed inside the hollow tube 81 so that the surface of the shutter 87a is perpendicular to the first direction. In addition, the lens 86 is fixed so that the optical axis of the lens 86 is parallel to the first direction, as in the first embodiment.

The half mirror 88 reflects the incident light at predetermined reflectance that is less than 100%, such as 10% in this embodiment, and transmits 90% of the incident light. Accordingly, 90% of the red, green, and blue laser beams emitted from the emission end of the illumination fiber 73 pass through the half mirror 88, while the other 10% of the red, green, and blue laser beams emitted from the emission end of the illumination fiber 73 are reflected by the half mirror 88.

The red, green, and blue laser beams that pass through the half mirror 88 reach the first liquid crystal shutter 67a. The first liquid crystal shutter 87a either transmits or blocks the incident light on the basis of the control of the LC driver 28. The transmitting and blocking of the incident light are described later.

Figure 12:
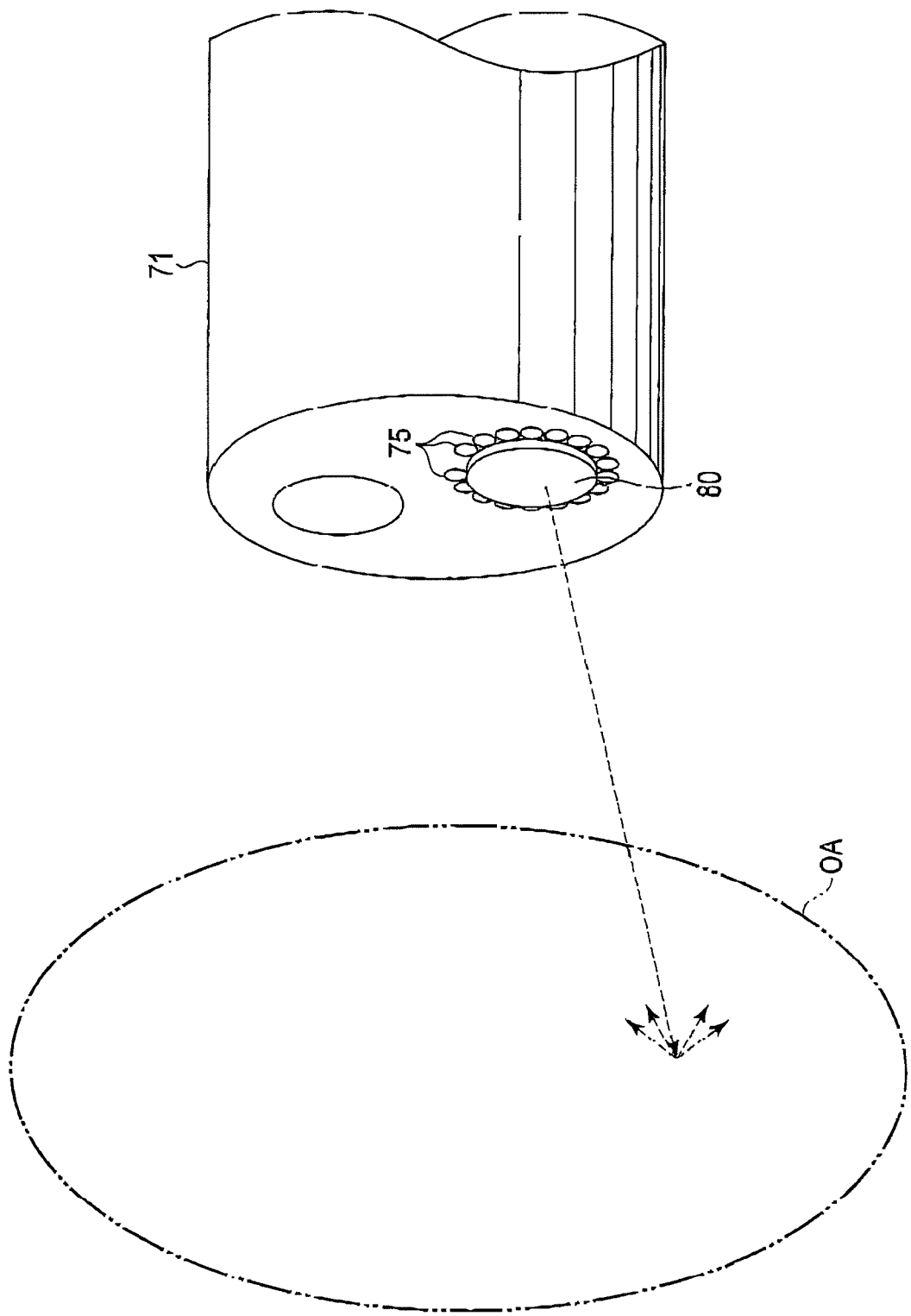
FIG. 12 illustrates the condition when light is emitted from the lens.

The red, green, and blue laser beams that pass through the first liquid crystal shutter 87a also pass through the lens 86 before illuminating a point within the observation area (see FIG. 12). At the point illuminated by the red, green, and blue laser beams, light is scattered and reflected toward the incident ends of the image fibers 75.

The arrangement of the image fibers 75 at the incident end is the same as in the first embodiment. The light that is scattered and reflected from the point in the observation area is incident on all the image fibers 75, as in the first embodiment.

The reflected light incident on the incident ends of the image fibers 75 is transmitted to the emission ends the image fibers 75. As described above, the emission ends of the image fibers 75 are optically connected to the light-capturing unit 50. The reflected light transmitted to the emission ends is incident on the light-capturing unit 50.

An opening 81h is formed in the side of the hollow tube 81 where the laser beams are reflected by the half mirror 88. The position detection filter 830, the condenser lens 84, and the second liquid crystal shutter 87b are fixed inside the opening 81h.

The shape and arrangement of the position detection filter 830 are the same as in the first embodiment. The arrangement of the condenser lens 84 is also the same as in the first embodiment. In addition, the second liquid crystal shutter 87b is fixed so that the surface of the shutter 87b is parallel to the first and second directions.

Figure 19:
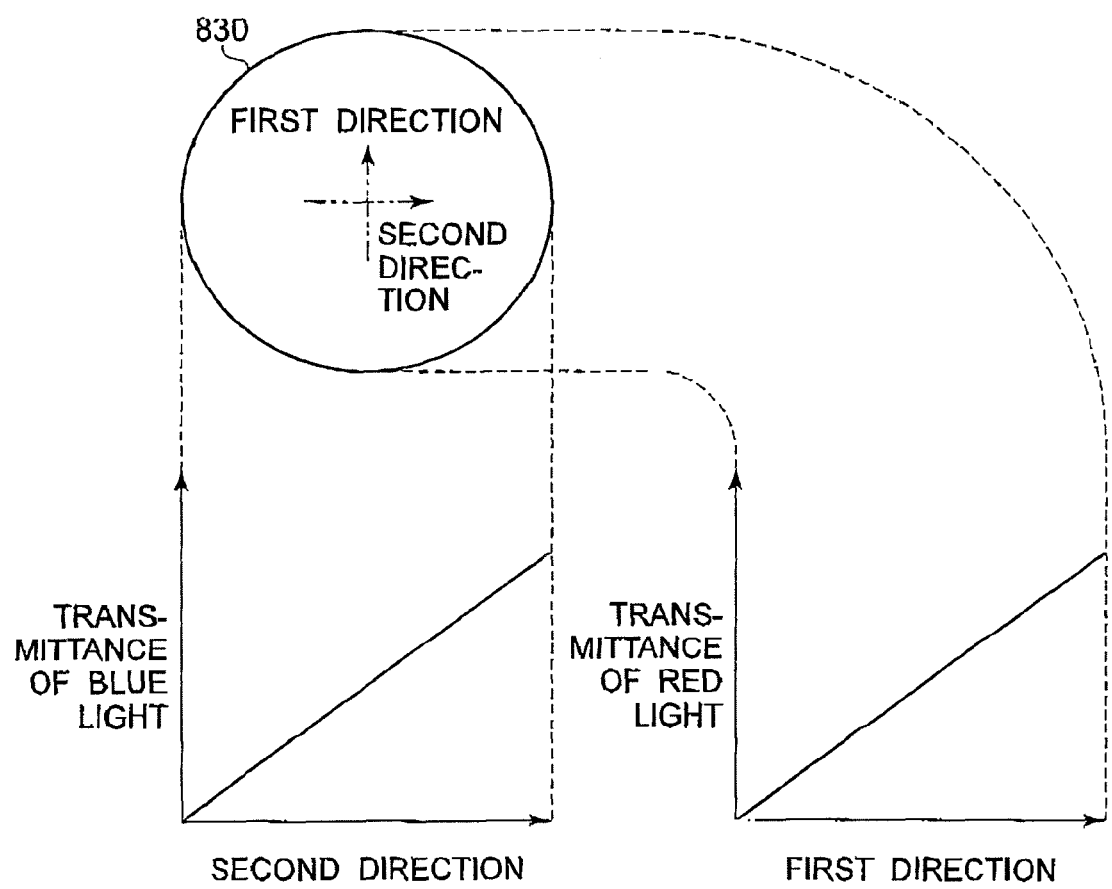
FIG. 19 is a graph illustrating the optical property of the position detection filter of the second and third embodiments.

The position detection filter 830 transmits red and blue light at varying transmittance levels according to the position of the position detection filter 830 on which light is incident. As shown in FIG. 19, the position detection filter 830 is formed so that the transmittance of the red light increases as the illuminated position of the position detection filter 830 moves toward the first direction. In addition, the position detection filter 830 is formed so that the transmittance of the blue light increases as the illuminated position of the position detection filter 830 moves toward the second direction.

The red and blue laser beams reflected by the half mirror 88 pass through the position detection filter 830, and are condensed by the condenser lens 84. The arrangement of the mirror 85 is the same as in the first embodiment.

The second liquid crystal shutter 87b is mounted between the condenser lens 84 and the mirror 85. The second liquid crystal shutter 87b either transmits or blocks the incident light on the basis of the control of the LC driver 28.

The incident end of the position detection fiber 76 is oriented toward the direction from which the red and blue laser beams are reflected by the mirror 85. The red and blue laser beams that are incident on the position detection fiber 76 are transmitted to the light-capturing unit 50 by the position detection fiber 76.

Figure 20:
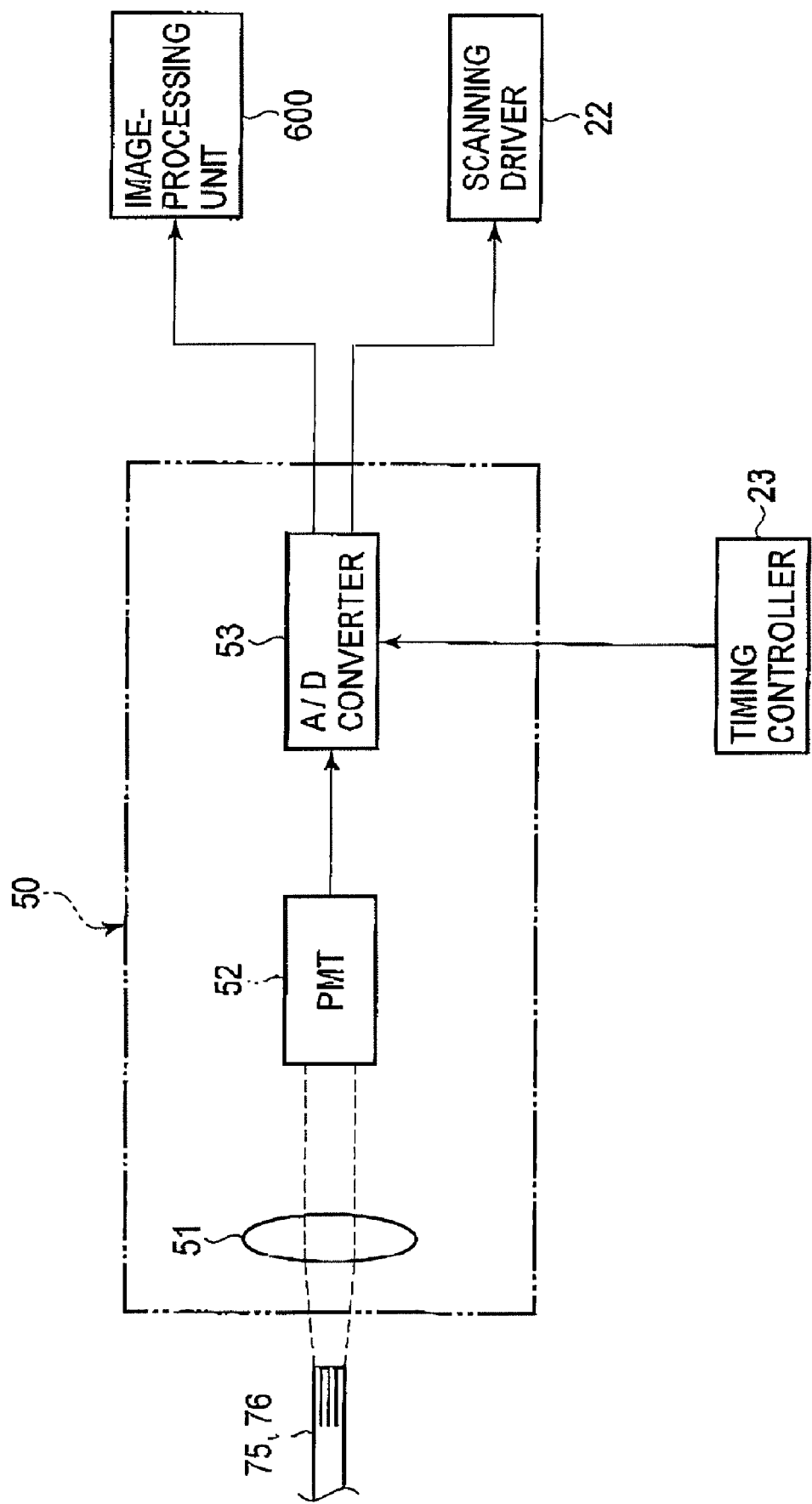
FIG. 20 is a block diagram schematically showing the internal structure of the light-capturing unit of the second embodiment.

As shown in FIG. 20, the light-capturing unit 50 comprises a collimating lens 51, a photoelectric converter 52, and an A/D converter 53. The emission ends of the image fibers 75 and the position detection fiber 76 are bundled together. The bundled emission ends are optically connected to the light-capturing unit 50. The collimating lens 51 and the photoelectric converter 52 are mounted in the direction that faces the light emitted from the bundled emission ends.

The red, green, and blue light emitted from the bundled emission ends passes through the collimating lens and reaches the photoelectric converter 52. The photoelectric converter 52 is a photomultiplier tube, as in the first embodiment. The photoelectric converter 52 generates a light-quantity signal according to the amount of the red, green, and blue light that it receives. The light-quantity signals are digitized by the A/D converter 53.

The timing controller 23 controls the timing of the light-capturing unit 50 when it generate the light-quantity signal so that the light-quantity signal is coordinated with both the light-on and -off timing of the light-source unit 300 and the timing of the first and second liquid crystal shutter 87a and 87b for transmitting and blocking light.

Figure 21:
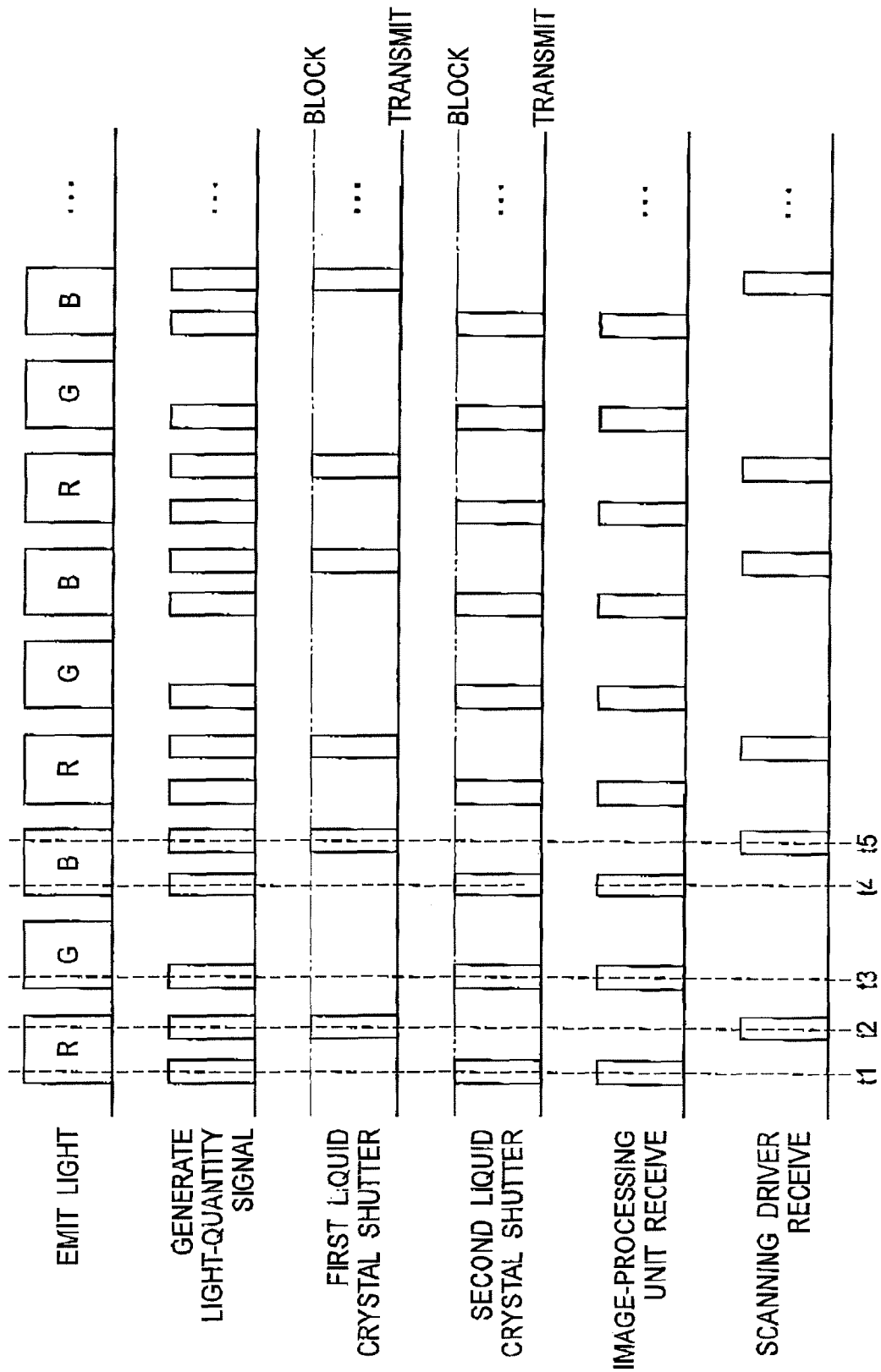
FIG. 21 is a timing chart showing the operations of the light-source unit, the light-capturing unit, the first and second liquid crystal shutters, the image-processing unit, and the scanning drivers in the second embodiment.

As shown in FIG. 21, the timing controller 23 orders the light-source unit 300 to repeatedly emit the red, green, and blue light (first light) in order. While the light-source unit 300 is emitting the red light, the timing controller 23 orders the light-capturing unit 50 to generate two separate light-quantity signals at two different times (see "t1" and "t2").

In addition, at time t1 when the first light-quantity signal is generated during emission of the red light, the timing controller 23 controls the LC driver 28 so that the first and second liquid crystal shutters 87a and 87b transmit and block light, respectively. Meanwhile, the timing controller 23 orders the image-processing unit 50 to receive the generated light-quantity signal as a pixel signal.

In addition, at time t2 when the second light-quantity signal is generated during emission of the red light, the timing controller 23 controls the LC driver 28 so that the first and second liquid crystal shutters 87a and 87b block and transmit light, respectively. In addition, the timing controller 23 orders the scanning driver 22 to receive the generated light-quantity signal as a position signal.

While the light-source unit 30 is emitting the green light, the timing controller 23 orders the light-capturing unit 50 to generate a light-quantity signal only once (see "t3"). In addition, at time t3 when the green light is omitted and the light-quantity signal is generated, the timing controller 23 controls the LC driver 28 so that the first and second liquid crystal shutters 87a and 87b transmit and block light, respectively. The timing controller 23 also orders the image-processing unit 50 to receive the generated light-quantity signal as a pixel signal.

While the light-source unit 30 is emitting the blue light, the timing controller 23 orders the light-capturing unit 50 to generate two separate light-quantity signals at two different times (see "t4" and "t5"), as in the case when red light is emitted.

In addition, at time t4 when the first light-quantity signal is generated during emission of the blue light, the timing controller 23 controls the LC driver 28 so that the first and second liquid crystal shutters 87a and 87b transmit and block light, respectively. The timing controller 23 also orders the image-processing unit 50 to receive the generated light-quantity signal as a pixel signal.

In addition, at time t5 when the second light-quantity signal is generated during emission of the blue light, the timing controller 23 controls the LC driver 28 so that the first and second liquid crystal shutters 87a and 87b block and transmit light, respectively. The timing controller 23 also orders the scanning driver 22 to receive the generated light-quantity signal as a position signal.

As described above, when the light-quantity signal used for the pixel signal is generated, the point of illumination in the observation area receives light transmitted from the first liquid crystal shutter 87a, and then reflects the received light to the image fibers 75. In addition, the position detection fiber 76 is blocked from incident light by the second liquid crystal shutter 87b. Accordingly, the light-capturing unit 60 receives only the light reflected from the illuminated point within the observation area.

On the other hand, when the light-quantity signal that is used for the position signal is generated, the image fibers 75 are blocked from incident light by the first liquid crystal shutter 87a. In addition, a quantity of light according to the position of the emission end of the illumination fiber 73 is transmitted by the second liquid crystal shutter 87b and made incident on the position detection fiber 76. Accordingly, the light-capturing unit 60 receives only the light passing through the position detection filter 830.

Figure 22:
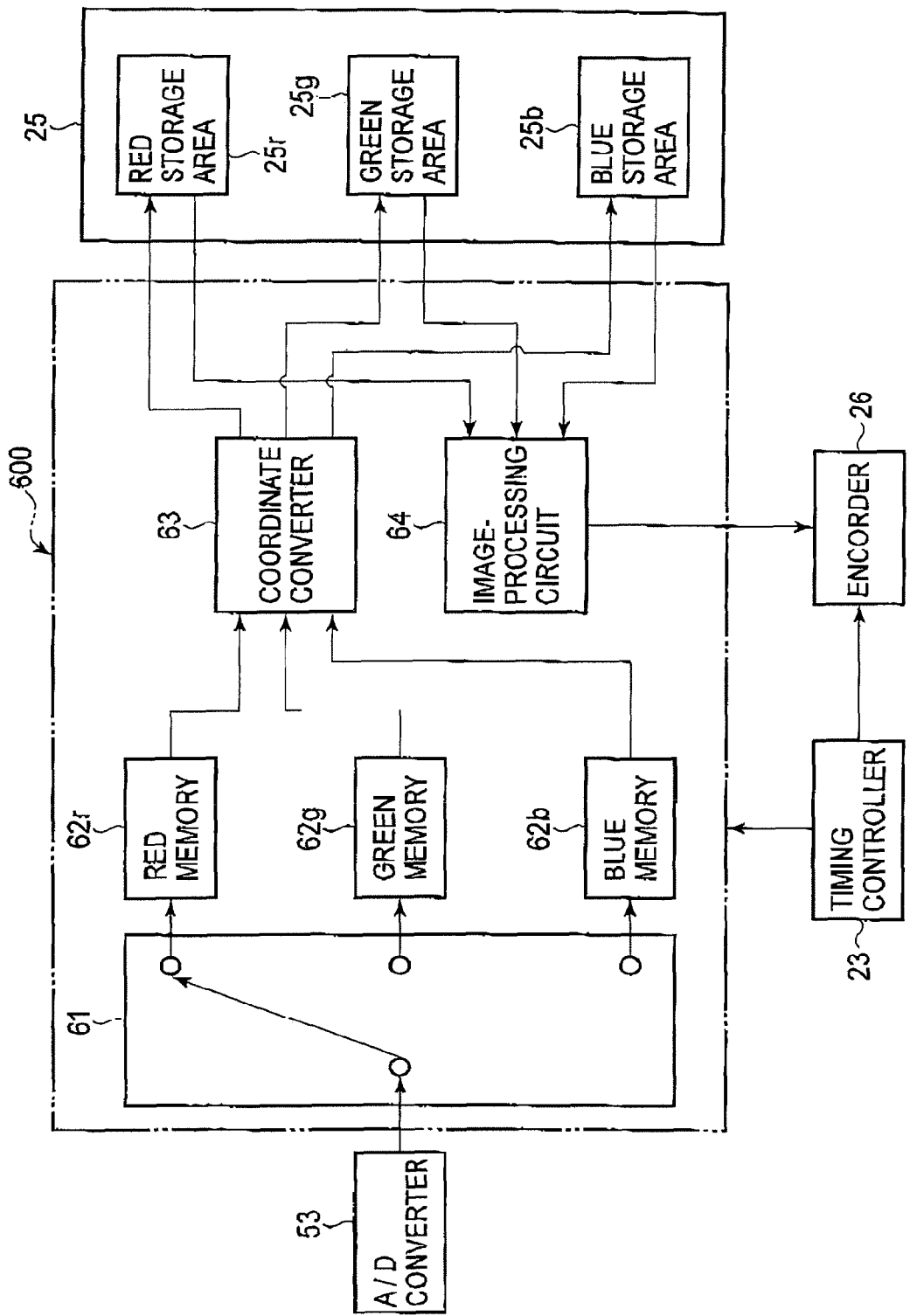
FIG. 22 is a block diagram schematically showing the internal structure of the image-processing unit of the second and third embodiments.

As shown in FIG. 22, the image-processing unit 600 comprises a selector 61; red, green and blue memories 62r, 62g and 62b; a coordinate converter 63; and an image-processing circuit 64.

The pixel signal output from the A/D converter 53 is transmitted to and stored in either one of the red, green, or blue memory 62r, 62g, or 62b. The timing controller 23 controls the selector 61 as it transmits the pixel signal received when the red light is shined (see "t1" in FIG. 21) toward the red memory 62r, and the pixel signal is stored in the red memory 62r. Similarly, the selector 61 transmits the pixel signal received when the green light is shined (see "t3" in FIG. 21) toward the green memory 62g, and the pixel signal is stored in the green memory 62g. Likewise the selector 61 transmits the pixel signal received when the blue light is shined (see "t4" in FIG. 21) toward the blue memory 62b, and the pixel signal is stored in the blue memory 62b.

Figure 23:
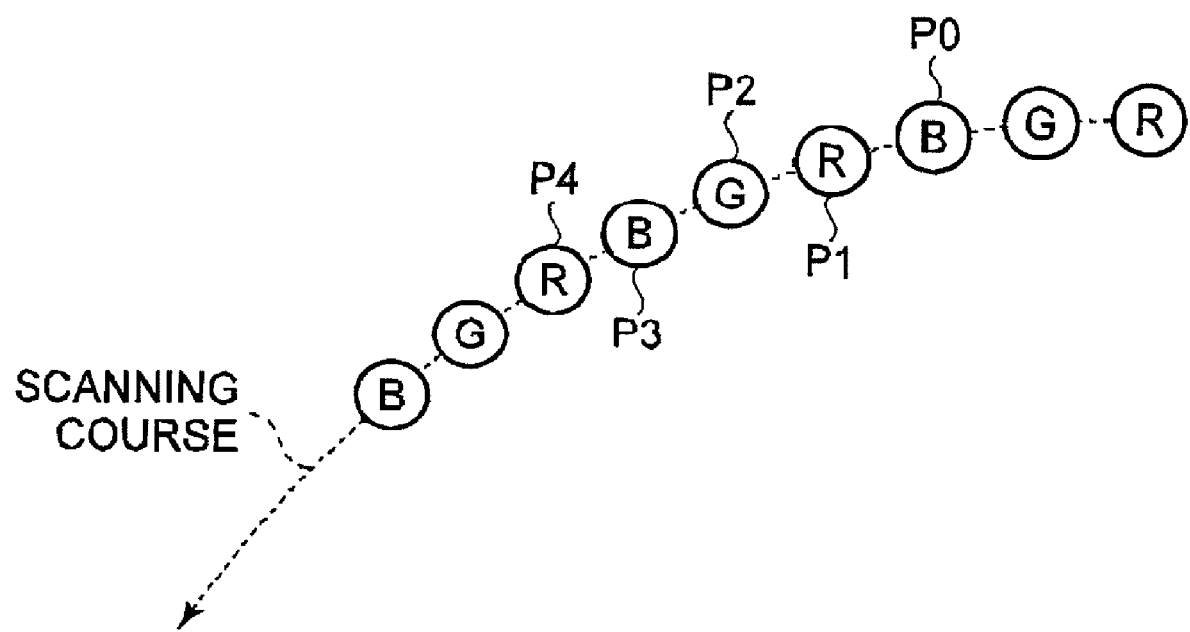
FIG. 23 illustrates the different kinds of light illustrated on each point on the course for scanning.

As shown in FIG. 23, either one of the red, green, or blue light is shined on each point of the scanning course. Accordingly, each pixel signal has signal intensity according to the amount of red, green, or blue light component at each illuminated point.

For example, the pixel signal generated when the red light is shined on the first point (see "P1") corresponds to the red-pixel signal component at the first point. The pixel signal generated when the green light is shined on the second point (see "P2") corresponds to the green-pixel signal component at the second point. The pixel signal generated when the blue light is shined on the third point (see "P3") corresponds to the blue-pixel signal component at the third point.

On the other hand, blue- and green-pixel signal components are not generated at the first point; red- and blue-pixel signal components are not generated at the second point; and red- and green-pixel signal components are not generated at the third point.

In order to compensate for different colored pixel signal components than the color actually shined on each point, a pixel signal component for any other color is used as a pixel signal at points adjacent to the point in question.

For example, for the first point a pixel signal generated at the first point, a pixel signal generated at the next illuminated point, (i.e., the second point), and a pixel signal generated at the previous illuminated point are used as red-, green-, and blue-pixel signal components, respectively.

Similarly, for the second point, pixel signals generated at the first, second, and third points are used as red-, green-, and blue-pixel signal components, respectively.

The image memory 25 comprises red, green and blue storage areas 25r, 25g, and 25b, for storing the red-, green- and blue-pixel signal components, respectively (see FIG. 22). The red, green, and blue storage areas 25r, 25g, and 25b have addresses corresponding to the points illuminated by either red, green, or blue light. For example, each one of storage areas 25r, 25g, and 25b have an address corresponding to the first point.

When a pixel signal is stored in the red memory 62r, the coordinate converter 63 reads out the pixel signal from the red memory 62r and stores the pixel signal in the red storage area 25r at three separate addresses corresponding to the point illuminated with the red light, the point immediately before the point illuminated with the red light, and the point immediately after the point illuminated with the red light. The illuminated point is estimated on the basis of the position control signal.

For example, when a pixel signal generated for the first point is stored in the red memory 62r, the coordinate converter 63 reads out the pixel signal from the red memory 62r. Then, the coordinate converter 63 stores the pixel signal generated for the first point in the red storage area at addresses corresponding to the first point (see "P1" in FIG. 23), the point immediately before the first point (see "P0") and the second point (see "P2").

Similarly, when a pixel signal is stored in the green memory 62g, the coordinate convertor 63 reads out the pixel signal from the green memory 62g, and stores the pixel signal in the green storage area 25g at three separate addresses corresponding to the point illuminated with the green light, the point immediately before the point illuminated with the green light, and the point immediately after the point illuminated with the green light.

For example, when a pixel signal generated for the second point is stored in the green memory 62g, the coordinate converter 63 reads out the pixel signal from the green memory 62g. Then, the coordinate converter 63 stores the pixel signal generated for the second point in the green storage area 25g at addresses corresponding to the first, second, and third points (see "P1", "P2", and "P3").

Similarly, when a pixel signal is stored in the blue memory 62b, the coordinate converter 63 reads out the pixel signal from the blue memory 62b, and stores the pixel signal in the blue storage area 25b at three separate addresses corresponding to the point illuminated with the blue light, the point immediately before the point illuminated with the blue light, and the point immediately after the point illuminated with the blue light.

For example, when a pixel signal generated for the third point is stored in the blue memory 62g, the coordinate converter 63 reads out the pixel signal from the blue memory 62b. Then, the coordinate converter 63 stores the pixel signal generated for the third point in the blue storage area 25b at addresses corresponding to the second point, third point, and the fourth point that immediately follows the third point, (see "P2", "P3", and "P4").

After storing the pixel signals from the scan-start point (i.e., the standard point) to the scan-end point in the image memory 25, the image-processing circuit 64 reads out all pixel signals stored at all of the addresses of the red, green and blue storage areas 25r, 25g, and 25b as one frame of an image signal.

The image-processing circuit 64 carries out predetermined image processing on the image signal before the image signal, having undergone predetermined image processing, is transmitted to the encoder 26.

As described above, the position signal is transmitted from the A/D converter 53 to the scanning driver 22. As explained below, the position signal is used to correct for movement of the emission end of the illumination fiber 73.

As explained in the first embodiment, it is necessary for the emission end of the illumination fiber 73 to precisely trace the predetermined spiral course. However, the moving emission end may be off of the spiral course.

The scanning driver 22 determines the actual position of the moving emission end of the illumination fiber 73 on the basis of successively received position signals. In addition, the scanning driver 22 determines whether or not the emission end of the illumination fiber 73 is off of the predetermined spiral course. If the emission end is off of the spiral course, the scanning driver 22 generates the fiber driving signal, which is adjusted to make the emission end return to the spiral course, and transmits the adjusted fiber driving signal to the fiber actuator 74.

In the second embodiment, the position of the emission end of the illumination fiber 73 can be determined. In addition, even if the emission end of the illumination fiber 73 is off of the predetermined spiral course, the distortion of a complete image can be reduced by making a correction that restores the course of the moving emission end to the predetermined spiral course.

In addition, in the second embodiment, the structure can be simplified and the manufacturing cost can be reduced because a single photoelectric converter 52 generates a pixel signal and a position signal.

In the second embodiment, it is difficult to accurately pinpoint the point illuminated by the light used for capturing an image. However, the points neighboring the point illuminated by the light used for capturing an image can be determined. Consequently, the point illuminated by the light for capturing an image can be determined approximately.

Next, a scanning endoscope apparatus of the third embodiment is explained. The primary difference between the third embodiment and the second embodiment is the structures or the had end unit and the scanning endoscope processor. The third embodiment is explained mainly with reference to the structures that differ from those of the second embodiment. Here, the same index numbers are used for the structures that correspond to those of the first and second embodiments.

Figure 24:
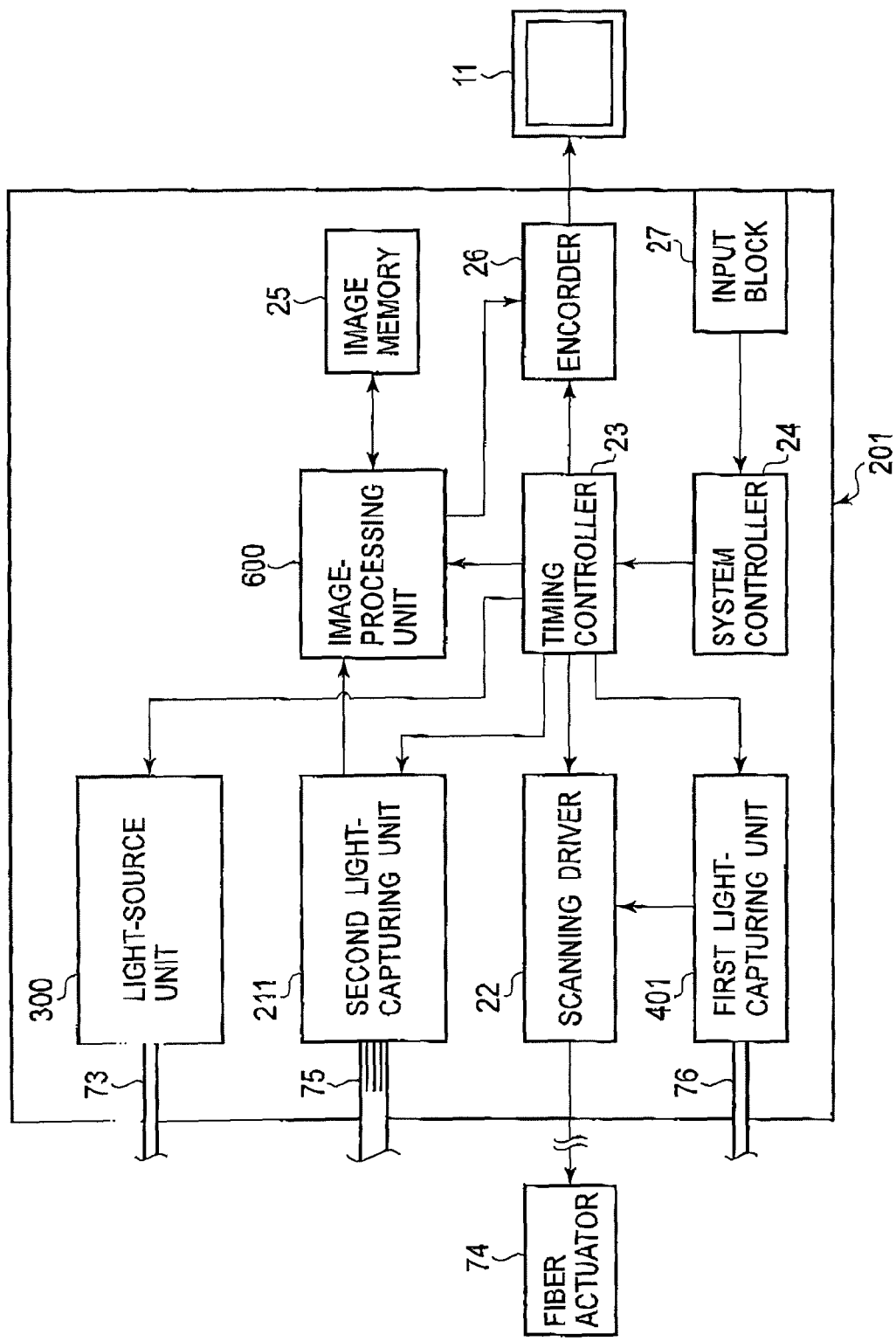
FIG. 24 is a block diagram schematically showing the internal structure of the scanning endoscope processor of the third embodiment.

As shown in FIG. 24, the scanning endoscope processor 201 comprises a light-source unit 300, first and second light-capturing units 401 and 211, a scanning driver 22, an image-processing unit 600, a timing controller 23, a system controller 24, and other components, as in the first embodiment.

By connecting the scanning endoscope 701 to the scanning endoscope processor 201, optical connections are made between the light-source unit 300 and the illumination fiber 73, between the second light-capturing unit 211 and the image fibers 75, and between the first light-capturing unit 40 and the position detection fiber 76, as in the first embodiment.

In addition, by connecting the scanning endoscope 701 to the scanning endoscope processor 201, the fiber actuator 74 is electrically connected with the scanning driver 22, as in the first embodiment.

The structure and function of the light-source unit 300 are the same as those in the second embodiment. Accordingly, the light-on and -off timing for red, green, and blue light is controlled by the timing controller 23.

The structure of the scanning endoscope 701—except for the head end unit 801—and the emission ends of the image fibers 75 and the position detection fiber 76 are the same as those in the second embodiment.

Figure 25:
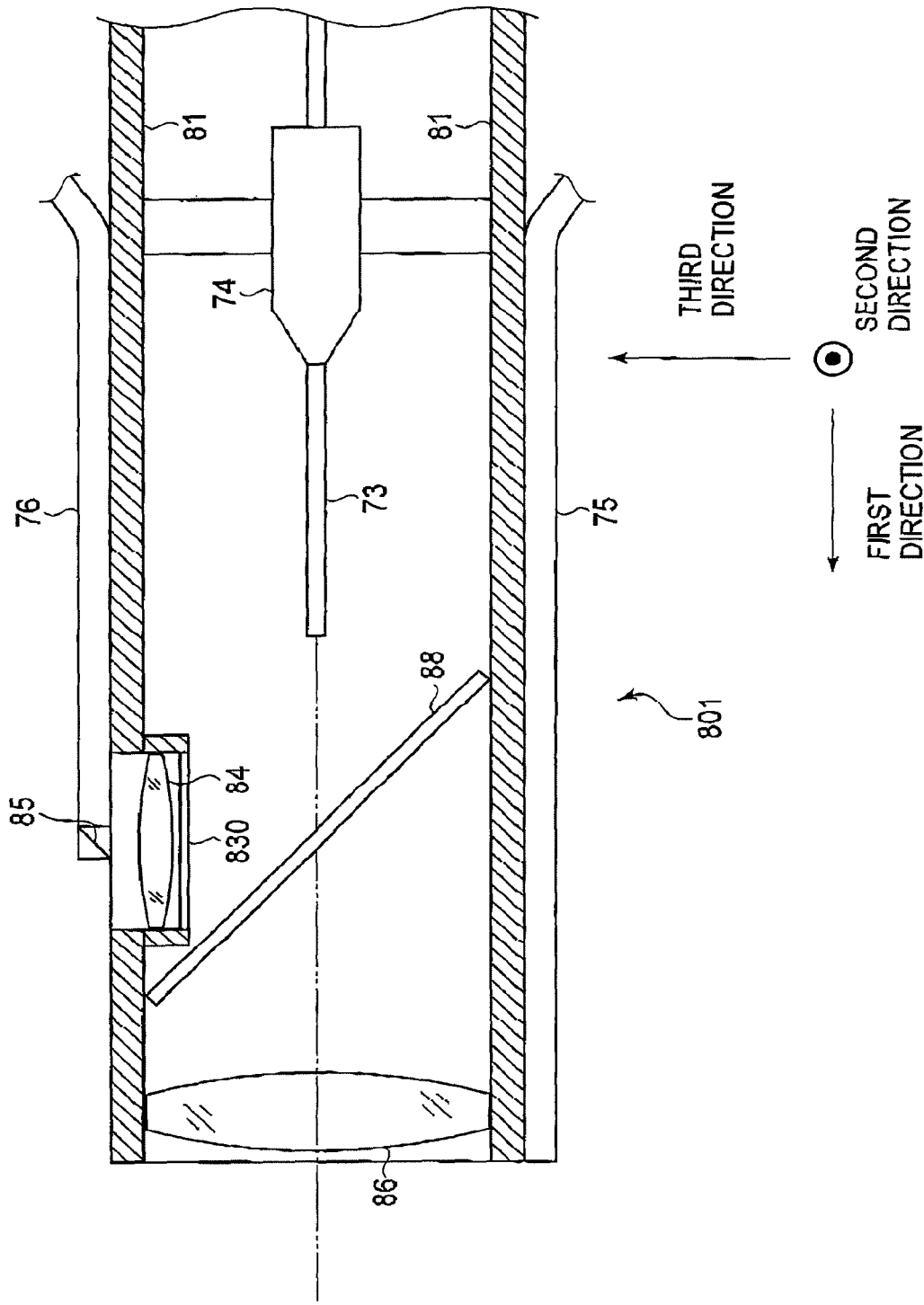
FIG. 25 is a structural diagram showing a cut-away view of the internal structure of the head end unit of the third embodiment.

As shown in FIG. 25, the head end unit 801 comprises a hollow tube 81, the fiber actuator 74, a position detection filter 830, a condenser lens 84, a mirror 85, a lens 86, and a half mirror 88, as in the second embodiment. The head end unit 801 does not comprise the first and second liquid crystal shutters, unlike in the second embodiment.

The structures, arrangement, and functions of the hollow tube 81, the fiber actuator 74, the position detection filter 830, the condenser lens 84, the mirror 85, the lens 86, and the half mirror 88 are the same as those in the first embodiment.

Consequently, when light is emitted from the emission end of the illumination fiber 73, 90% of the emitted light passes through the half mirror 88 and reaches the observation area. The light reflected from the point of illumination is incident on the incident ends of the image fibers 75, and transmitted to the second light-capturing unit 211.

In addition, when light is emitted from the emission end of the illumination fiber 73, 10% of the emitted light is reflected by the half mirror 88 toward the position detection filter 830. As shown in FIG. 19, the transmittance of the red light increases as the illuminated position of the position detection filter 830 moves in the first direction, as in the second embodiment. In addition, the transmittance of the blue light increases as the illuminated position of the position detection filter 830 moves in the second direction, as in the second embodiment. The red and blue light that passes through the position detection filter 830 is incident on the incident end of the position detection fiber 76, and transmitted to the first light-capturing unit 400.

The second light-capturing unit 211 generates a pixel signal according to the amount of light transmitted by the image fibers 75. The intensity of the generated pixel signal corresponds to the amount of either the red, green, or blue light, as in the second embodiment. The pixel signal is digitized and transmitted to the image-processing unit 60.

Figure 26:
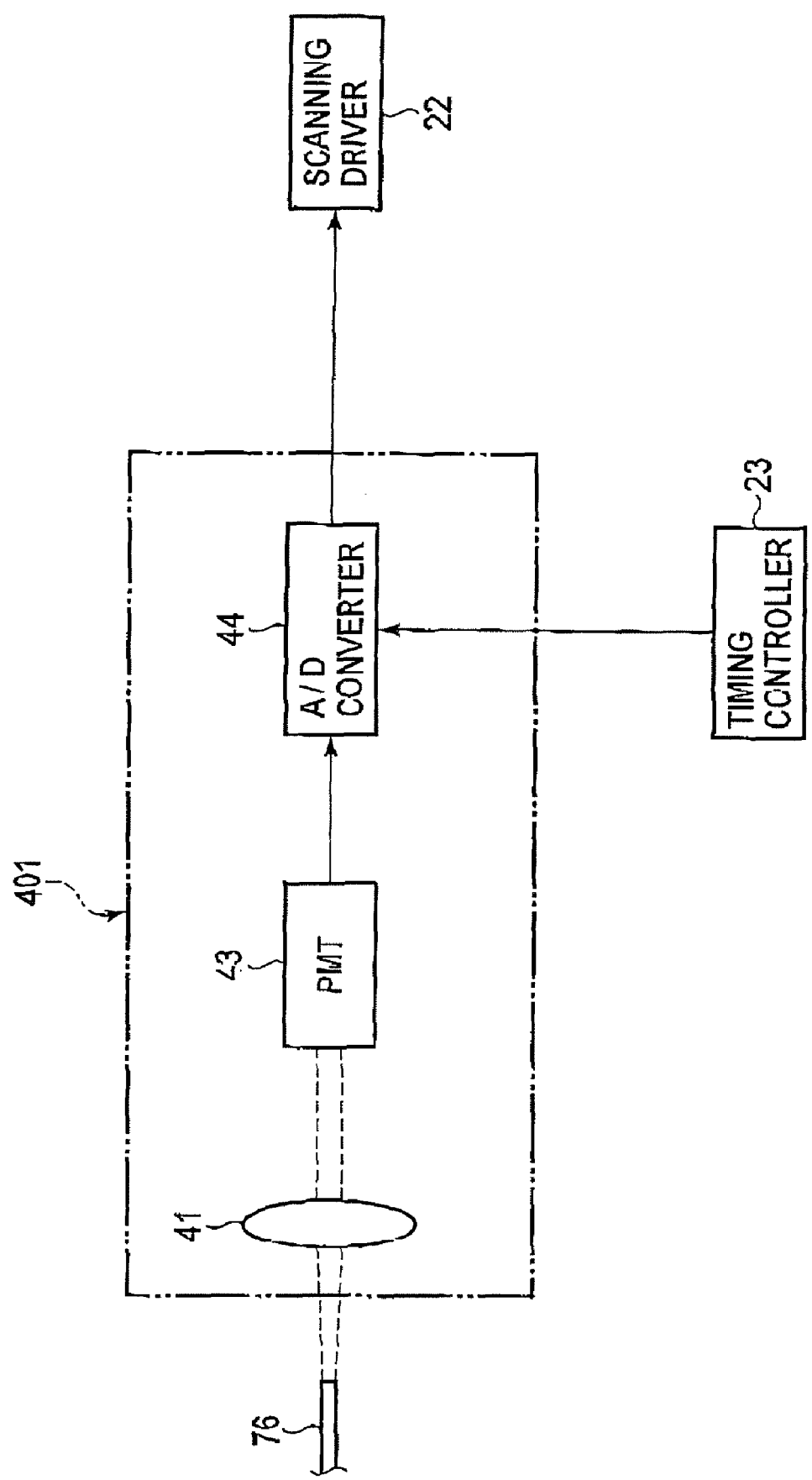
FIG. 26 is a block diagram schematically showing the internal structure of the first light-capturing unit of the third embodiment.

As shown in FIG. 26, the first light-capturing unit 401 comprises a collimating lens 41, a photoelectric converter 43, and an A/D converter 44. The red, green, and blue light emitted from the emission end of the position detection fiber 76 passes through the collimating lens 41 and is made incident on the first light-capturing unit 401. The photoelectric converter 43 is a photomultiplier tube that generates a position signal with a signal intensity that corresponds to the amount of red, green, and blue light received. The position signal is digitized by the A/D converter 44. The position signal is transmitted to the scanning driver 22 after being digitized.

The timing controller 23 controls the timing of both the second light-capturing unit 211 and the first light-capturing unit 401 to generate the pixel signal and position signal, respectively, so that the timing of generating the pixel signal and the position signal are each related to the light-on and -off timing of the light-source unit 300.

As shown in FIG. 27, the timing controller 23 orders the light-source unit 300 to repeatedly emit red, green, and blue light in order. While the light-source unit 300 is emitting the red light, the timing controller 23 orders the first and second light-capturing units 401 and 211 to generate a pixel signal (see "t1") and a position signal (see "t2"), respectively, at different points in time.

While the light-source unit 300 is emitting the green light, the timing controller 23 orders the second light-capturing unit 211 to generate a pixel signal (see "t3").

While the light-source unit 300 is omitting the blue light, the timing controller 23 orders the first and second light-capturing units 401 and 211 to generate a pixel signal (see "t4") and a position signal (see "t5"), respectively, at different points in time.

The structure and function of the image-processing unit 600 are the same as in the second embodiment. Accordingly, the imago-processing unit 600 stores pixel signals in the red, green, and blue storage areas 25$r$, 25$g$, and 25$b$ at three separate addresses predetermined for the point of illumination. One frame of an image signal is generated by storing pixel signals corresponding to all of the illuminated points, from the scan-start point to the scan-end point, as in the second embodiment.

The position signal is transmitted to the scanning driver 22. The scanning driver 22 determines the moving position of the emission end of the illumination fiber 73 and makes the emission end return to the spiral course, as in the second embodiment.

In the third embodiment, the position of the emission end of the illumination fiber 73 can be determined. The course which the emission end of the illumination fiber 73 traces can be corrected so that it is aligned with the predetermined spiral course. In addition, the structure of the third embodiment can be simplified and its manufacturing cost reduced with respect to the second embodiment, because the first and second liquid crystal shutters are not mounted in the third embodiment, unlike in the second embodiment.

In addition, it is difficult to accurately pinpoint the point illuminated by the light used for capturing an image. However, the point illuminated by the light used for capturing an image can be determined approximately, as in the second embodiment.

The first and second directions, in which the transmittance varies according to the position that the light is made incident upon, are perpendicular to each other in all three embodiments. However, the two directions do not have to be perpendicular to each other as long as they at least intersect one another. In order to easily control the fiber actuator 74, it is preferable that the transmittance varies according to the position that the light is made incident upon in the direction of the light reflected by ell-her the beam splitter 82 or the half mirror 88, when the emission end of the illumination fiber 73 is bended separately by the first and second bending elements 74$b$1 and 74$b$2.

The transmittance of the position detection filter varies in two different directions in all three embodiments. However, the transmittance may vary according to the position that light is made incident upon in any number of different directions or one direction only. If the transmittance varies in only one direction, only positions corresponding to movements in the direction in which the transmittance varies are detectable. However, in a general scanning endoscope in a prior art, the position of the emission end of the illumination fiber 73 was estimated on the basis of the fiber driving signal, which is used by the fiber actuator 74 to move the illumination fiber 73. In comparison to such a scanning endoscope in a prior art, the accuracy of the estimated position of the emission end can be increased by determining the precise position in only one direction.

The emission end of the illumination fiber 73 is moved so that the emission end traces the spiral course in all three embodiments. However, the observation area can be scanned with a laser beam even if the emission end is moved along a different course.

The red, green, blue, first and second infrared laser beams are emitted from the light-source unit 30, as in the above first embodiment. And the red, green, and blue laser beams are emitted from the light-source unit 300, as in the above second and third embodiments. The light-source unit 30 and 300 may emit other kinds of light, such as excitation light that excites an organ to fluoresce. Then, autofluorescence incident on the incident end of the image fibers 75 can be transmitted to the second light-capturing unit 21 and 211 or the light-capturing unit 50, and the image can be produced on the basis of the autofluorescence.

Lasers are used as light sources to emit red, green, blue, first and second infrared light in the above first embodiment, and to emit red, green, and blue light in the above second and third embodiments. However, other kinds of light sources may be used. But, a laser is preferable for the light source in the above embodiments because of its ability to shine the illumination light having strong directivity on a minute point within an observation area of the scanning endoscope.

When the emission end of the illumination fiber 73 traces off of the predetermined spiral course, an adjustment is made in all three embodiments. However, the course traced by the emission end may not need to be adjusted to the predetermined spiral course. A user can observe the image produced by the pixel signals that are generated without correcting the course traced by the emission end. In addition, a distortion can be reduced by image processing using the positions determined on the basis of the first and second position signals.

The first and second infrared laser beams, of which the bands do not overlap, are emitted from the first and second infrared lasers 31$i$1 and 31$i$2, respectively, in the above first embodiment. However, an infrared laser that can emit an infrared laser beam with a wide band that encompasses both the third and fourth bands can be adopted instead of the first and second infrared lasers 31*i*1 and 31*i*2.

The infrared light is used for detecting the position of the emission end of the illumination fiber 73 in the above first embodiment. However, any other kinds of light, such as ultraviolet light or visible light can be used. The same effect can be achieved as long as a beam splitter reflects the light used for detecting the position while transmitting the light having the other band.

If pixel signals at illuminated points on the predetermined spiral course are not genera. Led in a certain frame, pixel signals in the previous frame are used for the illuminated points at which the pixel signals were not generated, in the above first embodiment. However, even though the moving emission end of the illumination fiber 73 could be positioned anywhere, all of the pixel signals that are generated in a certain frame can be used for producing an image. As described above, a user can observe the image produced by using all of the pixel signals generated in a certain frame. In addition, distortion can be reduced by image processing using the first and second position signals.

The transmittance of red and blue light varies for the position detection filter 83 and 830 in the second and third embodiments. However, the transmittance for bands of light other than red and blue light can vary as well.

Although the embodiments of the present invention have been described herein with reference to the accompanying drawings, obviously many modifications and changes may be made by those skilled in this art without departing from the scope of the invention.

The invention claimed is:

1. A scanning endo scope apparatus comprising:
    a first transmitter that transmits light received at a first incident end to a first emission end, the first transmitter emitting a beam of the light exiting the first emission end;
    an actuator that moves the first emission end in a direction perpendicular to an emission direction, the beam of the exiting light being emitted from the first emission end in the emission direction;
    a first light source unit that emits light of a first band toward the first incident end;
    a first optical filter that is mounted in the optical path of the light emitted from the first emission end, the first optical filter reflecting the light of the first band, the first optical filter transmitting light of a second band, the second band being outside of the first band;
    a second optical filter that is mounted in the optical path of the light of the first band that is reflected by the first optical filter, the second optical filter transmitting the light of the first band at a transmittance that varies according to a position on a surface of the second optical filter where the light of the first band is incident;
    a second transmitter that receives the light of the first band, which has passed through the second optical filter, and transmits the received light from a second incident end to a second emission end;
    a first photo-detector that detects an amount of the light of the first band that is emitted from the second emission end; and
    a position determiner that determines a position of the first emission end on the basis of the amount of the light of the first band that is detected by the first photo-detector.

2. The scanning endo scope apparatus according to claim 1, wherein,
    the first light source emits light of third and fourth bands, the third and fourth bands being included in the first band and being different from each other,
    a transmittance of the light of the third band varies according to a position on the surface of the second optical filter where the light of the third band is incident in a first direction,
    a transmittance of the light of the fourth band varies according to a position on the surface of the second optical filter where the light of the fourth band is incident in a second direction, the second direction being different from the first direction,
    the first photo-detector comprises first and second detectors, the first and second detectors detecting amounts of the light of the third and fourth bands, respectively,
    the position determiner determines the position of the first emission end in a third direction on the basis of the amount of the light of the third band that is detected by the first detector, the third direction corresponding to the first direction, and
    the position determiner determines the position of the first emission end in a fourth direction on the basis of the amount of the light of the fourth band that is detected by the second detector, the fourth direction corresponding to the second direction.

3. The scanning endo scope apparatus according to claim 2, wherein the first light source comprises two light sources that emit the light of the third and fourth bands, respectively.

4. The scanning endo scope apparatus according to claim 1, further comprising:
    a second light source that emits the light of the second band, the light of the second band illuminating an observation area;
    a third transmitter that receives reflected light or fluorescence at a third incident end from the observation area illuminated by the light of the second band, the light of the second band being made incident on the first incident end by the second light source unit and emitted from the first emission end before passing through the first optical filter, the third transmitter transmitting the reflected light or fluorescence, which is incident on a third incident end, from the third incident end to a third emission end;
    a second photo-detector that generates a pixel signal according to an amount of light emitted from the third emission end;
    a memory that comprises addresses corresponding to different positions of the first emission end, the memory storing the pixel signals; and
    an image producer that commands the memory to store the pixel signal at an address of the memory that corresponds to the position of the first emission end that is determined by the position determiner when the second photo-detector generates the pixel signal.

5. The scanning endo scope apparatus according to claim 4, further comprising a scanning driver that controls the actuator to move the first emission end along a predetermined course,
    the image producer producing a first frame of an image signal by storing a plurality of pixel signals at addresses in the memory that correspond to the positions of the first emission end, the pixel signals corresponding to reflected light or fluorescence from a plurality of small areas within the observation area that are illuminated with the light of the second band emitted from a plurality of positions of the emission end along the predetermined course, the image producer updating the pixel signals of addresses corresponding to positions of the moving first emission end that are on the predetermined course when a second frame of the image signal is generated, the second frame being the next frame after the first frame, the second frame of the image signal being generated with both the updated pixel signals and pixel signals that are not updated from the first frame.

6. The scanning endo scope apparatus according to claim 1, further comprising:
a scanning driver that controls the actuator to move the first emission end along a predetermined course; and
a corrector that commands the actuator to move the first emission end when the position of the first emission end is determined by the position determiner to be off of the predetermined course, so that an actual position of the moving first emission end returns to the predetermined course.

7. The scanning endo scope apparatus according to claim 1, further comprising a condenser lens that condenses the light of the first band that has passed through the second optical filter, the condenser lens emitting the condensed light of the first band toward the second incident end.

8. The scanning endo scope apparatus according to claim 1, wherein the first band is outside of the band of visible light.

9. The scanning endo scope apparatus according to claim 1, further comprising a hollow tube that has a hole which penetrates through a lateral wall surface of the hollow tube,
wherein the first transmitter, the actuator and the first optical filter are provided inside of the hollow tube,
the second optical filter is provided inside of the hole, and
the second transmitter is provided outside of the hollow tube.

10. The scanning endo scope apparatus according to claim 9, further comprising a mirror that is provided on an optical path from the second optical filter to the second incident end of second transmitter,
wherein the mirror receives the light from the second optical filter and reflects the light to the second incident end of the second transmitter.

11. A scanning endo scope comprising:
a first transmitter that transmits light received at a first incident end to a first emission end, the first transmitter emitting a beam of the light exiting the first emission end;
an actuator that moves the first emission end in a direction perpendicular to an emission direction, the beam of the exiting light being emitted from the first emission end in the emission direction;
a first optical filter that is mounted in the optical path of the light emitted from the first emission end, the first optical filter reflecting light of a first band, the first optical filter transmitting light of a second band, the second band being outside of the first band;
a second optical filter that is mounted in the optical path of the light of the first band that is reflected by the first optical filter, the second optical filter transmitting the light of the first band at a transmittance that varies according to a position on a surface of the second optical filter where the light of the first band is incident; and
a second transmitter that receives the light of the first band, which has passed through the second optical filter, and transmits the received light from a second incident end to a second emission end.

12. A scanning endoscope processor that is connected with the scanning endoscope according to claim 11, the scanning endoscope processor comprising:
a first light source unit that emits the light of the first band toward the first incident end;
a first photo-detector that detects an amount of the light of the first band that is emitted from the second emission end; and
a position determiner that determines a position of the first emission end on the basis of the amount of the light of the first band that is detected by the first photo-detector.

13. A scanning endoscope apparatus comprising:
a light source that emits first light;
a first transmitter that transmits the first light emitted from the light source from a first incident end to a first emission end, the first transmitter emitting a beam of the first light exiting the first emission end;
an actuator that moves the first emission end in a direction perpendicular to an emission direction, the beam of the exiting first light being emitted from the first emission end in the emission direction;
a third optical filter that is mounted in the optical path of the first light emitted from the first emission end, the third optical filter reflecting a part of the first light, the third optical filter transmitting a part of the first light;
a fourth optical filter that is mounted in the optical path of the first light reflected by the third optical filter, the fourth optical filter transmitting the first light at a transmittance that varies according to a position on a surface of the fourth optical filter where the first light is incident;
a second transmitter that receives the first light, which has passed through the fourth optical filter, and transmits the received first light from a second incident end to a second emission end; and
a third transmitter that receives reflected light or fluorescence from an observation area that has been illuminated with the first light that has passed through the third optical filter at a third incident end, the third transmitter transmitting the reflected light or fluorescence from the third incident end to a third emission end,
a pixel signal being generated for the observation area according to an amount of the first light or fluorescence that is emitted from the third emission end,
a position of the first emission end being determined on the basis of an amount of the first light emitted from the second emission end.

14. The scanning endo scope apparatus according to claim 13, wherein,
the light source separately emits second and third light, which are included in the first light, the second and third light being different from each other,
a transmittance of the second light varies according to a position on the surface of the fourth optical filter where the second light is incident in a first direction,
a transmittance of the third light varies according to a position on the surface of the fourth optical filter where the third light is incident in a second direction, the second direction being different from the first direction,
the position of the first emission end in a third direction is determined on the basis of the amount of the second light that is emitted from the second emission end when the second light of the light source is on and the third light is off, the third direction corresponding to the first direction, and
the position of the first emission end in a fourth direction is determined on the basis of the amount of the third light that is emitted from the second emission end when the second light of the light source is off and the third light is on, the fourth direction corresponding to the second direction.

15. The scanning endo scope apparatus according to claim 13 wherein,
the light source separately emits second, third, and fourth light, the first light including the second and third light, the second, third, and fourth light being different from each other,
an image corresponding to an entire observation area is produced on the basis of second, third, and fourth pixel signals, the second pixel signal being generated according to an amount of the second light or fluorescence emitted from the third emission end when the second light of the light source is on and the third and fourth light is off, the third pixel signal being generated according to an amount of the third light or fluorescence emitted from the third emission end when the second and fourth light of the light source is off and the third light is on, the fourth pixel signal being generated according to an amount of the fourth light or fluorescence emitted from the third emission end when the second and third light of the light source is off and the fourth light is on.

16. The scanning endo scope apparatus according to claim 13, further comprising:
a scanning driver that controls the actuator to move the first emission end along a predetermined course; and
a corrector that commands the actuator to move the first emission end when the determined position of the first emission end is off of the predetermined course, so that an actual position of the moving first emission end returns to the predetermined course.

17. The scanning endo scope apparatus according to claim 13, further comprising a condenser lens that condenses the first light that has passed through the fourth optical filter, the condenser lens emitting the condensed first light toward the second incident end.

18. The scanning endo scope apparatus according to claim 13, further comprising:
a first shutter that alternately transmits and blocks the first light that has passed through the third optical filter, the first light transmitted by the first shutter being directed to the observation area;
a second shutter that alternately transmits and blocks the first light reflected by the third optical filter, the first light transmitted by the second shutter being directed to the second incident end;
a third photo-detector that generates a light-quantity signal according to an amount of light emitted from the second and third emission ends;
a position determiner that determines the position of the first emission end on the basis of the light-quantity signal;
an image producer that produces an image corresponding to a complete observation area on the basis of the light-quantity signal; and
a controller that repeatedly performs first and second operations, in the first operation, the first shutter, the second shutter, and the position determiner being controlled to block the first light, to transmit the first light, and to determine the position of the first emission end, respectively, and in the second operation, the first shutter, the second shutter, and the image producer being controlled to transmit the first light, to block the first light, and to produce the image, respectively.

19. The scanning endo scope apparatus, according to claim 13, further comprising:
a first photo-detector that generates a position signal according to the amount of the first light emitted from the second emission end;
a position determiner that determines a position of the first emission end on the basis of the position signal;
a second photo-detector that generates a pixel signal according to the amount of the first light or fluorescence emitted from the third emission end; and
an image producer that produces an image corresponding to an entire observation area on the basis of the pixel signal.

20. The scanning endo scope apparatus according to claim 13, further comprising a hollow tube that has a hole which penetrates through a lateral wall surface of the hollow tube,
wherein the first transmitter, the actuator and the third optical filter are provided inside of the hollow tube,
the fourth optical filter is provided inside of the hole, and
the second transmitter and the third transmitter are provided outside of the hollow tube.

21. The scanning endo scope apparatus according to claim 20, further comprising a mirror that is provided on an optical path from the fourth optical filter to the second incident end of the second transmitter,
wherein the mirror receives the light from the fourth optical filter and reflects the light to the second incident end of the second transmitter.

22. A scanning endoscope comprising:
a first transmitter that transmits first light from a first incident end to a first emission end, the first transmitter emitting a beam of the first light exiting from the first emission end;
an actuator that moves the first emission end in a direction perpendicular to an emission direction, the beam of the exiting first light being emitted from the first emission end in the emission direction;
a third optical filter that is mounted in the optical path of the first light emitted from the first emission end, the third optical filter reflecting a part of the first light, the third optical filter transmitting a part of the first light;
a fourth optical filter that is mounted in the optical path of the first light reflected by the third optical filter, the fourth optical filter transmitting the first light at a transmittance that varies according to a position on a surface of the fourth optical filter where the first light is incident;
a second transmitter that receives the first light, which has passed through the fourth optical filter, and transmits the received first light from a second incident end to a second emission end; and
a third transmitter that receives reflected light or fluorescence from an observation area that has been illuminated with the first light that passes through the third optical filter at a third incident end, the third transmitter transmitting the reflected light or fluorescence from the third incident end to a third emission end.

23. A scanning endoscope processor that is connected to the scanning endoscope according to claim 22, the scanning endoscope processor comprising a light source that emits the first light toward the first incident end, a pixel signal being generated for the observation area according to an amount of the first light or fluorescence that is emitted from the third emission end, a position of the first emission end being determined on the basis of an amount of the first light emitted from the second emission end.

* * * * *